(12) United States Patent
Pouillot et al.

(10) Patent No.: US 11,957,724 B2
(45) Date of Patent: *Apr. 16, 2024

(54) PHAGE THERAPY OF *E COLI* INFECTIONS

(71) Applicant: ERYTECH PHARMA, Lyons (FR)

(72) Inventors: Flavie Pouillot, Paris (FR); Hélène Blois, Paris (FR)

(73) Assignee: ERYTECH PHARMA, Lyons (FR)

( * ) Notice: Subject to any disclaimer, the term of this patent is extended or adjusted under 35 U.S.C. 154(b) by 384 days.

This patent is subject to a terminal disclaimer.

(21) Appl. No.: 17/038,442

(22) Filed: Sep. 30, 2020

(65) Prior Publication Data

US 2021/0060100 A1  Mar. 4, 2021

Related U.S. Application Data

(63) Continuation of application No. 15/110,769, filed as application No. PCT/EP2015/050355 on Jan. 9, 2015, now Pat. No. 10,918,680.

(30) Foreign Application Priority Data

Jan. 10, 2014  (EP) ................... 14305041

(51) Int. Cl.
*A61K 35/76* (2015.01)
*A01N 63/40* (2020.01)
(Continued)

(52) U.S. Cl.
CPC .............. *A61K 35/76* (2013.01); *A01N 63/40* (2020.01); *C07K 14/005* (2013.01); *C12N 7/00* (2013.01); *C12Q 1/18* (2013.01); *G01N 33/56916* (2013.01); *C12N 2795/00021* (2013.01); *C12N 2795/00022* (2013.01); *C12N 2795/00031* (2013.01); *C12N 2795/00032* (2013.01); *C12N 2795/00071* (2013.01); (Continued)

(58) Field of Classification Search
None
See application file for complete search history.

(56) References Cited

U.S. PATENT DOCUMENTS 10,077,431 B2    9/2018  Pouillot et al.
10,918,680 B2 *  2/2021  Pouillot ........... G01N 33/56916
(Continued)

FOREIGN PATENT DOCUMENTS

CN   1699560    11/2005
CN   101724607   6/2010
(Continued)

OTHER PUBLICATIONS

JN986846 Enterobacteria phage vB_EcoM_ACG-C40, complete genome (Year: 2012).*
(Continued)

*Primary Examiner* — Michelle S Horning
(74) *Attorney, Agent, or Firm* — SALIWANCHIK, LLOYD & EISENSCHENK

(57) ABSTRACT

The present invention relates to bacteriophage therapy. More particularly, the present invention relates to novel bacteriophages having a high specificity against *Escherichia coli* strains, their manufacture, components thereof, compositions comprising the same and the uses thereof in phage therapy.

13 Claims, 4 Drawing Sheets

Specification includes a Sequence Listing.

(51) Int. Cl.
  *C07K 14/005* (2006.01)
  *C12N 7/00* (2006.01)
  *C12Q 1/18* (2006.01)
  *G01N 33/569* (2006.01)

(52) U.S. Cl.
  CPC .............. *C12N 2795/10121* (2013.01); *C12N 2795/10122* (2013.01); *C12N 2795/10131* (2013.01); *C12N 2795/10132* (2013.01); *C12N 2795/10171* (2013.01); *C12N 2795/10221* (2013.01); *C12N 2795/10222* (2013.01); *C12N 2795/10231* (2013.01); *C12N 2795/10232* (2013.01); *C12N 2795/10271* (2013.01); *G01N 2333/245* (2013.01); *G01N 2800/52* (2013.01)

(56) References Cited

U.S. PATENT DOCUMENTS

| | | |
|---|---|---|
| 2017/0319637 A1 | 11/2017 | Pouillot et al. |
| 2019/0002840 A1 | 1/2019 | Pouillot et al. |

FOREIGN PATENT DOCUMENTS

| | | |
|---|---|---|
| CN | 101220349 | 2/2011 |
| CN | 103289963 | 9/2013 |
| EP | 2465926 | 6/2012 |
| JP | 2013-541333 | 11/2013 |
| WO | WO 02/07742 | 1/2002 |
| WO | WO 2009/075884 | 6/2009 |
| WO | WO 2012/036580 | 3/2012 |

OTHER PUBLICATIONS

JX536493.1 Enterobacteria phage HX01, complete genome (Year: 2012).*
EF056009 *Escherichia* phage N4, complete genome. (Year: 2006).*
Ceyssens, P.-J. et al. "Comparative analysis of the widespread and conserved PB1-like viruses infecting *Pseudomonas aeruginosa*" *Environmental Microbiology*, 2009, pp. 2874-2883, vol. 11, No. 11.
Alemayehu, D. et al. "Bacteriophages ΦMR299-2 and ΦNH-4 Can Eliminate *Pseudomonas aeruginosa* in the Murine Lung and on Cystic Fibrosis Lung Airway Cells" *MBIO*, Mar. 6, 2012, pp. 1-9, vol. 3, No. 2, Article No. e0002912.
Fu, W. et al. "Bacteriophage Cocktail for the Prevention of Biofilm Formation by *Pseudomonas aeruginosa* on Catheters in an In Vitro Model System" *Antimicrobial Agents and Chemotherapy*, Jan. 1, 2010, pp. 397-404, vol. 54, No. 1.
Fukuda, K. et al. "*Pseudomonas aeruginosa* Keratitis in Mice: Effects of Topical Bacteriophage KPP12 Administration" *PLOS One*, Oct. 2012, pp. 1-8, vol. 7, No. 10, Article No. e47742.
Garbe, J. et al. "Characterization of JG024, a pseudomonas aeruginosa PB1-like broad host range phage under simulated infection conditions" *BMC Microbiology*, Nov. 26, 2010, pp. 1-10, vol. 10, No. 1.
Krylov, V. et al. "A Genetic Approach to the Development of New Therapeutic Phages to Fight *Pseudomonas aeruginosa* in Wound Infections" *Viruses*, Dec. 21, 2012, pp. 15-53, vol. 5.
Mcvay, C.S. et al. "Phage Therapy of *Pseudomonas aeruginosa* Infection in a Mouse Burn Wound Model" *Antimicrobial Agents and Chemotherapy*, Jun. 2007, pp. 1934-1938, vol. 51, No. 6.
Oikonomou, O. et al. "Investigation of carbapenem heteroresistance among different sequence types of *Pseudomonas aeruginosa* clinical isolates reveals further diversity" *J. Med. Microbiology*, May 19, 2011, pp. 1556-1558, vol. 60, No. 10.
Wright, A. et al. "A controlled clinical trial of a therapeutic bacteriophage preparation in chronic otitis due to antibiotic-resistant *Pseudomonas aeruginosa*; a preliminary report of efficacy" *Clin. Otolaryngol.* 2009, pp. 349-357, vol. 34.
Database EMBL [Online] Accession No. FM887021, "Comparative analysis of the widespread and conserved PB1-like viruses infecting *Pseudomonas aeruginosa*" Dec. 16, 2008, pp. 1-36, XP-002718979.
Database EMBL [Online] Accession No. AM910650, "Analysis of the genome, proteome and transcriptome of Pseudomonas aeruginosa phage LUZ24" Nov. 27, 2007, pp. 1-26, XP-002718980.
Database EMBL [Online] Accession No. JN254801, "Bacteriophages PhiMR299-2 and PhiNH-4 Can Eliminate Pseudomonas aeruginosa in the Murine Lung and on Cystic Fibrosis Lung Airway Cells" Apr. 27, 2012, pp. 1-32, XP-055161973.
Database EMBL [Online] Accession No. EU716414, "Comparative analysis of the widespread and conserved PB1-like viruses infecting Pseudomonas aeruginosa" Jan. 6, 2009, pp. 1-39, XP-002718981.
Database EMBL [Online] Accession No. JN254800, "Bacteriophages PhiMR299-2 and PhiNH-4 Can Eliminate Pseudomonas aeruginosa in the Murine Lung and on Cystic Fibrosis Lung Airway Cells" Mar. 13, 2012, pp. 1-41, XP-002718982.
Database EMBL [Online] Accession No. GU815091, "Characterization of JG024, a pseudomonas aeruginosa PB1-like broad host range phage under simulated infection conditions" Dec. 16, 2010, pp. 1-64, XP-055162017.
Database EMBL [Online] Accession No. KC294142, "Pseudomonas aeruginosa phage PaP4" Jan. 16, 2013, pp. 1-29, XP-002718983.
Database EMBL [Online] Accession No. AB560486, "Pseudomonas aeruginosa Keratitis in Mice: Effects of Topical Bacteriophage KPP12 Administration" Aug. 23, 2012, pp. 1-35, XP-002718984.
Database EMBL [Online] Accession No. FM201282, "Genome and proteome analysis of newly isolated Pseudomonas aeruginosa phages" Aug. 22, 2008, pp. 1-37, XP-002718985.
Written Opinion in International Application No. PCT/EP2014/072905, dated Jan. 27, 2015, pp. 1-11.
Wang, I.-N., et al. "Holins: The Protein Clocks of Bacteriophage Infections" *Annu. Rev. Microbiol.* 2000, pp. 799-825 and supplemental pp. 1-6, vol. 54.
Reardon, S. "Phage therapy gets revitalized" *Nature*, Jun. 5, 2014, pp. 15-16, vol. 510.
Database EBI [Online] Accession No. FM897211, "Pseudomonas phage 14-1, complete genome" Dec. 14, 2008, pp. 1-2, XP-002738707.
Database EBI [Online] Accession No. KF856712, "Pseudomonas phage philBB-PAA2, complete genome" Dec. 4, 2013, p. 1, XP-002738709.
Database EBI [Online] Accession No. FM201281, "Pseudomonas phage LBL3 complete genome" Aug. 22, 2008, pp. 1-2, XP-002738708.
Written Opinion in International Application No. PCT/EP2015/075949, dated Jan. 14, 2016, pp. 1-8.
Database GenBank [Online] Accession No. JQ067092, "Pseudomonas phage PaMx42, complete genome" 2012, pp. 1-25.
Cuevas, J. M. et al. "Point Mutation Rate of Bacteriophage ΦX174" *Genetics*, Oct. 2009, pp. 747-749, vol. 183.
Ofir, G et al. "Contemporary Phage Biology: From Classic Models to New Insights" *Cell*, Mar. 8, 2018, pp. 1260-1270, vol. 172.
Carter, C.D. et al. "Bacteriophage cocktail significantly reduces *Escherichia coli* O157:H7 contamination of lettuce and beef, but does not protect against recontamination" *Bacteriophage*, Jul. 2012, pp. 178-185, vol. 2, No. 3.
Pouillot, F. et al. "Genetically Engineered Virulent Phage Banks in the Detection and Control of Emergent Pathogenic Bacteria" *Biosecurity and Bioterrorism: Biodefense Strategy, Practice, and Science*, Jun. 1, 2010, pp. 155-169, vol. 8, No. 2.
Stone, R. "Bacteriophage Therapy: Stalin's Forgotten Cure" *Science*, Oct. 25, 2002, pp. 728-731, vol. 298, No. 5594.
Database EMBL [Online] Accession No. M38308, "Bacteriophage T7 RNA polymerase gene, complete cds" Nov. 7, 1990, p. 1, XP-002725532.
Database EMBL [Online] Accession No. AY303349, "Enterobacteria phage RB69, complete genome" Jul. 1, 2003, pp. 1-58, XP-002725574.
Database EMBL [Online] Accession No. AY370674, "Enterobacteria phage K1-5, complete genome" Feb. 3, 2004, pp. 1-12, XP-002725533.
Database EMBL [Online] Accession No. AM084414, "Enterobacteria phage K1F, complete genome" Dec. 5, 2005, pp. 1-13, XP-002725538.
Database EMBL [Online] Accession No. EF056009, "Enterobacteria phage N4, complete genome" Nov. 15, 2006, pp. 1-18, XP-002725539.
Database EMBL [Online] Accession No. EU330206, "Enterobacteria phage phiEco32, complete genome" Jan. 5, 2008, pp. 1-25, XP-002725530.

(56) References Cited

OTHER PUBLICATIONS

Database EMBL [Online] Accession No. DQ832317, "*Escherichia coli* bacteriophage rv5, complete sequence" Jun. 30, 2008, pp. 1-42, XP-002725541.
Database EMBL [Online] Accession No. EU734171, "Enterobacteria phage BA14, complete genome" Jul. 2, 2008, pp. 1-13, XP-002725534.
Database EMBL [Online] Accession No. EU734174, "Enterobacteria phage 13a, complete genome" Jul. 2, 2008, pp. 1-14, XP-002725540.
Database EMBL [Online] Accession No. AZU35935, "Bacteriophage F488/08 genomic DNA, Seq ID 3" May 10, 2012, pp. 1-30, XP-002725537.
Database EMBL [Online] Accession No. JX128259, "*Escherichia* phage ECML-134, complete genome" Jul. 29, 2012, pp. 1-53, XP-002725536.
Database EMBL [Online] Accession No. JN986844, "Enterobacteria phage vB_EcoP_ACG-C91, complete genome" Nov. 1, 2012, pp. 1-13, XP-002725531.
Written Opinion in International Application No. PCT/EP2015/050355, dated May 6, 2015, pp. 1-12.
Drulis-Kawa, Z. et al. "Learning from Bacteriophages—Advantages and Limitations of Phage and Phage-Encoded Protein Applications" *Current Protein and Peptide Science*, 2012, pp. 699-722, vol. 13.
Database GenBank [Online] Accession No. JN986846.1, "Enterobacteria phage vB_EcoM_ACG-C40, complete genome" 2012, pp. 1-104.
Database GenBank [Online] Accession No. JX536493.1, "Enterobacteria phage HX01, complete genome" 2012, pp. 1-52.
Attwood, T. K. "The Babel of Bioinformatics" *Science*, Oct. 27, 2000, pp. 471-473, vol. 290, No. 5491.
Baker, D. et al. "Protein Structure Prediction and Structural Genomics" *Science*, Oct. 5, 2001, pp. 93-96, vol. 294, No. 5540.
Database Genbank [Online] Accession No. GQ468526.1, "Enterobacteria phage 285P, complete genome" 2010, pp. 1-18.
Database Genbank [Online] Accession No. AY264774.1, "Enterobacteria phage T7, complete genome" 2003, pp. 1-16.
Annex 1, Search Results from corresponding EP Application No. 15703227.7, dated Apr. 12, 2018, pp. 1-11.
Annex 2, Search Results from corresponding EP Application No. 15703227.7, dated Apr. 12, 2018, pp. 1-26.

\* cited by examiner

PHAGE THERAPY OF *E COLI* INFECTIONS

CROSS-REFERENCE TO RELATED APPLICATIONS

This application is a continuation of U.S. application Ser. No. 15/110,769, filed Jul. 11, 2016, which is the U.S. national stage application of International Patent Application No. PCT/EP2015/050355, filed Jan. 9, 2015.

The Sequence Listing for this application is labeled "Seq-List.txt" which was created on Jun. 24, 2016 and is 1552 KB. The entire content of the sequence listing is incorporated herein by reference in its entirety.

The present invention relates to novel bacteriophages, compositions comprising the same, their manufacture, and the uses thereof. The invention is particularly adapted for the treatment of an infection in a mammal and for improving a subject condition by modifying the flora in said subject.

BACKGROUND OF THE INVENTION

Bacteriophages (or phages) are small viruses displaying the ability to infect and kill bacteria while they do not affect cells from other organisms. Initially described almost a century ago by William Twort, and independently discovered shortly thereafter by Félix d'Herelle, more than 6000 different bacteriophages have been discovered and described morphologically, including bacterial and archeal viruses. The vast majority of these viruses are tailed while a small proportion are polyhedral, filamentous or pleomorphic. They may be classified according to their morphology, their genetic content (DNA vs. RNA), their specific host, the place where they live (marine virus vs. other habitats), and their life cycle. As intra-cellular parasites of bacterial cells, phages display different life cycles within the bacterial host: lytic, lysogenic, pseudo-lysogenic, and chronic infection (Weinbauer, 2004; Drulis-Kawa, 2012). Lytic phages cause lysis of the host bacterial cell as a normal part of their life cycles. Lysogenic phages (also termed temperate phages) can either replicate by means of the lytic life cycle and cause lysis of the host bacterium, or they can incorporate their DNA into the host bacterial DNA and become noninfectious prophages. Whatever the type of cycle of a phage life, the first step is the attachment to receptors of the bacterial cell wall before phages may enter the bacteria. This specific process influences the spectrum of the possible phage-bacteria interactions.

Bacteriophages are commonly used as research tools to modify bacteria in laboratory experiments.

Because of their target host cell specificity, the use of phages as a therapy to treat acute and chronic infections has been considered, particularly in dermatology, ophthalmology, urology, stomatology, pediatrics, otolaryngology or surgery. This concept of therapeutic use of phages to treat bacterial infection was, however, highly controversial from the very beginning and not widely accepted by the public or medical community. Early studies were widely criticized for lack of appropriate controls and inconsistent results. The lack of reproducibility and many conflicting results obtained in the various published studies led the Council on Pharmacy and Chemistry of the American Medical Association to conclude that the evidence for the therapeutic value of lytic filtrates was for the most part contradictory, unconvincing, and recommended additional research to confirm its purported benefits.

Since the introduction of antibiotics in the 1940s, little attention was paid to this field of therapeutics, especially in the Western world. But the extensive use of antibiotics has led to the widespread emergence and spread of antibiotic-resistant bacteria around the world, causing increasingly serious problems. It has therefore become a major therapeutic challenge to overcome the limited therapeutic options remaining to treat major multi-drug resistant microbes.

In addition, many pathogenic microorganisms reside within biofilms, which biofilms cause additional problems when designing new anti-microbial agents. In this regard, bacteria growing as a biofilm rather than in single-celled ("planktonic") forms tend to be particularly resistant to anti-microbial agents and to be particularly difficult for the host immune system to render an appropriate response.

*E. coli*, a Gram-negative, short rod-shaped bacterium belonging to the genus *Escherichia* and the family Enterobacteriaceae, shows high diversity and frequency in human or animal microbial flora. It was revealed that while most strains of *E. coli* are non-pathogenic, they can cause opportunistic infections. Furthermore, some *E. coli* strains are highly pathogenic and can cause diverse diseases and sepsis in mammals, including humans. Several reports associate the enterobacterium *Escherichia coli* with skin and soft tissue infections (SSTIs), one of the most common infections in patients of all age groups. In some moderate or severe cases, these infections require hospitalization and parenteral therapy. *E. coli* was notably found to be the causative agent of neonatal omphalitis (Fraser and al, 2006), cellulitis localized to lower or upper limbs (Brzozowski and al, 1997, Corredoira and al, 1994), necrotizing fasciitis (Afifi and al, 2008; Krebs and al, 2001), surgical site infections (Tourmousoglou and al, 2008), infections after burn injuries (Rodgers and al, 2000), and others. A study monitoring SSTIs during a 7-year period and encompassing three continents (Europe, Latin America, and North America) showed *E. coli* to be an important causative agent, since it was the third-most prevalent isolated species. *E. coli* therefore deserve specific and targeting therapy, especially taking into account the dramatic decline in antibiotic susceptibility of pathogenic *E. coli* strains in recent years, their diversity, and their substantial presence in microbial flora.

Furthermore, *E. coli* bacteria are able to form biofilms, contributing to their increased resistance to antibiotics. Such biofilms may comprise more than one type of bacteria supported and surrounded by an excreted extracellular matrix and assist bacteria to colonize various surfaces. Biofilms allow bacteria to attach to surfaces and to attain population densities which would otherwise be unsupportable, imparting increased resistance to not only antibiotics but many environmental stresses including toxins such as heavy metals, bleaches and other cleaning agents. It is known that bacteria within biofilms can be 100 to 1000 times more resistant to antibiotics than the same strain of bacteria growing in planktonic forms. Such an increased resistance means that bacteria that are apparently sensitive to antibiotics in a laboratory test may be resistant to therapy in a clinical setting. Even if some are cleared, biofilms may provide resistant reservoirs permitting rapid colonization once antibiotics are no longer present. It is therefore obvious that biofilms are major factors in many human diseases. Chemical treatments are unsuited to use against biofilms since this is precisely what they have evolved to counter. Physical abrasion does provide a mean to disrupt biofilms. Unfortunately, many surfaces where biofilms supports bacterial pathogenesis are poorly suited to rigorous abrasion, i.e. bones, joints, implanted medical devices, etc. For example, the surfaces of wounds or burns are extremely sensitive and delicate. Even where abrasion is both suitable and in routine use, clearing of biofilms is limited. Oral plaque on the surface of teeth is a biofilm and is partially cleared by regular brushing. However, bacteria are maintained on unbrushed surfaces (for example in the gaps between teeth) and can recolonize cleared surfaces both rapidly and effectively. From this, it is clear that existing approaches to clearing biofilms are of limited efficacy.

The capability for quick adaptation and their ability to form biofilms are the main reasons that identify *E. coli* as opportunistic pathogens. They have acquired the status of hospital pathogens, and may be isolated from clinical samples taken from the wounds, sputum, bladder, urethra, vagina, ears, eyes and respiratory tract. The emergence of resistance to the most powerful new antibiotics in such clinical *E. coli* strains, occurring even during treatment, makes the fight with *E. coli* hospital pathogens a great problem.

Furthermore, it has been reported that the pathological or physiological condition of a subject is influenced by the balance of microorganisms in the flora of the subject. Accordingly, modifying the microbial flora, or modifying said balance, or restoring said balance, by destroying *E. coli* population, is also a valuable approach for improving a subject condition.

Therefore, there is a great need for new antibacterial agents or compositions that can be used to destroy *E. coli* strains, even when organized in bacterial biofilms, suitable for use in human or animal therapy as well as for decontaminating materials.

SUMMARY OF THE INVENTION

The inventors have isolated and characterized new bacteriophages presenting specific lytic activity to *Escherichia coli* (*E. coli*), and which can be used as active agents in pharmaceutical or veterinary preparations, particularly to treat *E. coli* bacterial infections or to modify microbial balance in a subject. The new bacteriophages of the invention exhibit strong lytic activity, high selectivity, and can by combined to induce controlled destruction of a very large spectrum of *E. coli* cells.

An object of the invention is to provide antibacterial compositions comprising at least one, preferably at least two bacteriophages having lytic activity against an *Escherichia coli* strain, said bacteriophages being selected from the bacteriophages having a genome comprising a nucleotide sequence of anyone of SEQ ID NOs: 1 to 15 or a sequence having at least 90% identity thereto.

A further object of the present invention concerns a bacteriophage having lytic activity to an *Escherichia coli* strain, said bacteriophage having a genome comprising a nucleotide sequence selected from anyone of SEQ ID NOs: 1 to 15 or a sequence having at least 90% identity thereto, preferably at least 97% identity thereto. In a specific embodiment, the bacteriophages of the invention exhibit lytic activity to multi drug resistant strains, in particular to an antibiotic resistant pathogenic *E. coli*, such as, preferably Extended-Spectrum Beta-Lactamases (ESBL) strains or verotoxin-producing *E. coli* (VTEC) strains.

Another object of the invention relates to a bacteriophage which is selected from BP539, BP700, BP753, BP814, BP953, BP954, BP970, BP1002, BP1151, BP1155, BP1168, BP1176, BP1197, BP1226, or BP1229, having a genome comprising the nucleotide sequence of SEQ ID NOs: 1 to 15, respectively, and variants thereof, wherein said variants retain a phenotypic characteristic of said bacteriophage, and wherein said bacteriophage and variants thereof have lytic activity against an *E. coli* strain.

Another object of the invention resides in a composition comprising at least one bacteriophage as defined above. In a particular embodiment, the compositions of the invention comprise at least two distinct bacteriophages as defined above, preferably at least three, even more preferably at least four distinct bacteriophages as defined above. A specific composition of the invention comprises a combination of all of bacteriophages BP539, BP700, BP753, BP814, BP953, BP954, BP970, BP1002, BP1151, BP1155, BP1168, BP1176, BP1197, BP1226 and BP1229.

In another aspect, the invention is related to a bacteriophage having lytic activity to a pathogenic *E. coli* strain, wherein the bacteriophage is specific for *E. coli*, active against antibiotic-resistant *E. coli* strains, and has a productive lytic effect below 15.

The invention further concerns an isolated nucleic acid sequence contained in a bacteriophage of the invention, and an isolated polypeptide encoded by said isolated nucleic acid.

Another object of the invention is a composition comprising a polypeptide as defined above.

A further object of the invention is a composition comprising a nucleic acid as defined above.

The compositions of the invention typically further comprise a pharmaceutically or veterinary acceptable excipient or carrier. They may be liquid, semi-liquid, solid or lyophilized.

Another object of the invention relates to a bacteriophage, nucleic acid, polypeptide or composition as defined above, for use in the treatment of an infection in a mammal, for modifying the microbial flora in a mammal, for decontaminating a material and/or for killing an *E. coli* bacterium or for compromising the integrity of a bacterial biofilm.

The invention relates also to the use of one or several lytic bacteriophages to improve a subject condition by modifying the microbial flora in said subject. The microbial flora may be modified by correcting, adapting or restoring a proper balance of microorganisms in said flora.

The invention also relates to a method for treating an infection in a mammal, comprising the administration to said mammal of at least one bacteriophage, nucleic acid, polypeptide or composition as defined above.

The invention also relates to a method for treating a surface or material suspected of being contaminated with an *E. coli* bacterium, comprising applying to said surface or material at least one bacteriophage, nucleic acid, polypeptide or composition as defined above. The surface or material may be a surface of e.g., any device, vessel or laboratory material, cloth, etc.

Another object of the invention relates to a method for predicting or determining efficacy of a bacteriophage therapy in a subject, wherein the method comprises the step of determining in vitro a lytic activity of one or more bacteriophages of the invention to an *E. coli* strain from a sample of said subject, a lytic activity of one or more bacteriophages of the invention to at least one *E. coli* strain from said sample being indicative of an efficient treatment. The method further optionally comprises the step of treating the subject with at least one bacteriophage having a lytic activity to an *E. coli* strain from a sample of said subject.

In another aspect, the invention provides a method for selecting a subject or determining whether a subject is susceptible to benefit from a bacteriophage therapy, wherein the method comprises the step of determining in vitro a lytic activity of one or more bacteriophages of the invention to an E. coli strain from a sample of said subject, a lytic activity of one or more said bacteriophages of the invention to at least one E. coli strain being indicative of a responder subject.

The invention may be used in any mammal, preferably in human beings, or to treat any material, including laboratory materials or medical devices.

DETAILED DESCRIPTION OF THE INVENTION

Figure 1:
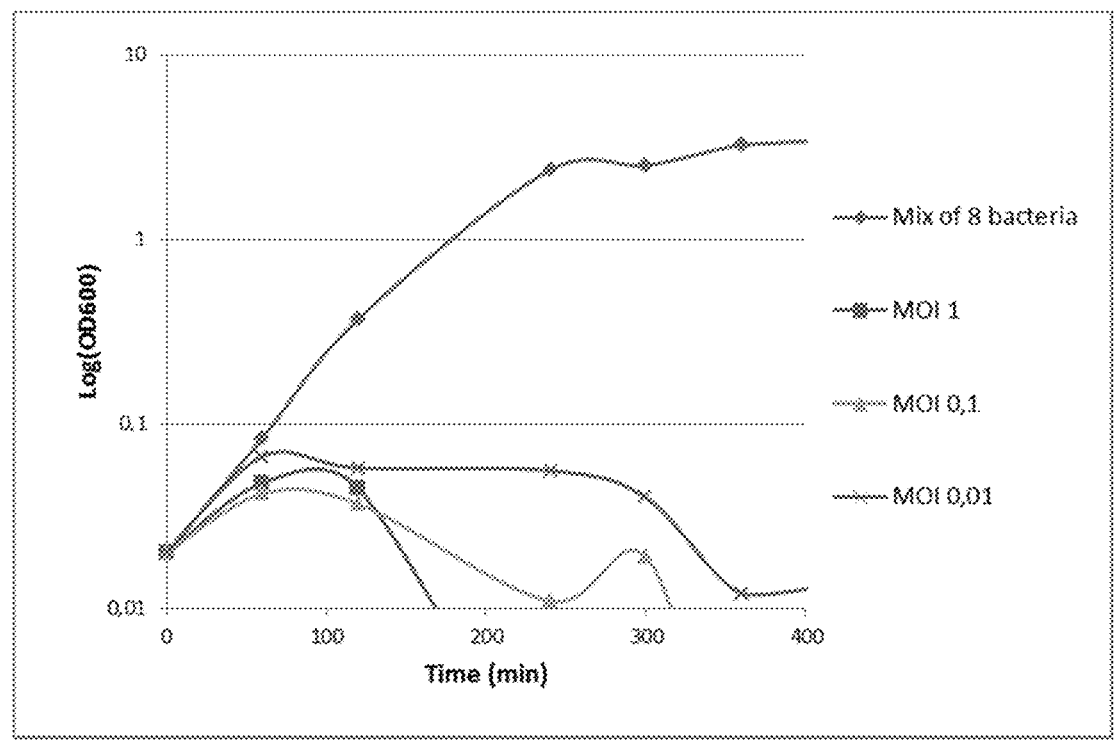
FIG. 1: In vitro efficiency of Bacteriophages of the invention on combinations of E. coli strains at various MOIs.

The present invention relates to novel bacteriophages, components thereof, compositions comprising the same, their manufacture, and the uses thereof as antibacterial agents, particularly for the treatment of an infection in a mammal and for improving a subject condition by modifying the microbial flora in said subject.

Definitions

To facilitate understanding of the invention, a number of terms are defined below.

As used herein, the term "bacteriophage" or "phage" refers to a functional phage particle comprising a nucleic acid genome packaged in a proteinaceous envelope or capsid. The term also refers to portions of the bacteriophage, including, e.g., a head portion, or an assembly of phage components, which provide substantially the same functional activity.

The term "phenotypic characteristic" designates more preferably the morphology and/or host-range of a bacteriophage. Methods for phenotyping bacteriophages are well known per se in the part and include, for example, determining bacterial host range and/or activity against the biofilm produced by certain bacterial strains.

The term "lytic activity" as used in the invention designates the property of a bacteriophage to cause lysis of a bacterial cell. The lytic activity of a bacteriophage can be tested on E. coli strains according to techniques known per se in the art (see also experimental section).

The term "variant" of a reference bacteriophage designates bacteriophages having variation(s) in the genomic sequence and/or polypeptide(s) encoded thereby as compared to said reference bacteriophage, while retaining the same phenotypic characteristic as the reference bacteriophage. Variants typically comprise e.g., silent mutations, conservative mutations, minor deletions, and/or minor replications of genetic material, and retain phenotypic characteristics of the reference bacteriophage. In a preferred embodiment, the variant of the invention retain any observable characteristic or property that is dependent upon the genome of the bacteriophage of the invention, i.e. phenotypic characteristics of said bacteriophage and/or lytic activity against the E. coli strains. Preferred variants have less than 5% nucleic acid variation as compared to the genome of the reference bacteriophage, even more preferably less than 4%, more preferably less than 2%. Alternatively, or in combination, variants have preferably less than 5% amino acid variation in a coded polypeptide sequence as compared to a polypeptide of the reference bacteriophage.

The term "% identity" in relation to nucleic acid sequences designates the level of identity or homology between said sequences and may be determined by techniques known per se in the art. Typically, the % identity between two nucleic acid sequences is determined by means of computer programs such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443-453). With settings adjusted to e.g., DNA sequences (particularly: GAP creation penalty of 5.0 and GAP extension penalty of 0.3), nucleic acid molecules may be aligned to each other using the Pileup alignment software available as part of the GCG program package.

The term "fragment" of a nucleic acid designates typically a fragment having at least 10 consecutive nucleotides of said nucleic acid, more preferably at least 15, 20, 25, 30, 35, 40, 50 or more consecutive nucleotides of said nucleic acid.

The term "fragment" of a polypeptide designates typically a fragment having at least 5 consecutive amino acids of said polypeptide, more preferably at least 10, 15, 20, 30, 40, 50 or more consecutive amino acids of said polypeptide.

The term "ESBL E. coli strain" refers to antibiotic-resistant E. coli, more specifically to Extended-Spectrum Beta-Lactamases-producing E. coli strains.

The term "VTEC" refers to another type of antibiotic-resistant E. coli strains, more specifically to verotoxin-producing E. coli strains.

The term "specific" or "specificity" in relation to a bacteriophage refers to the type of host that said bacteriophage is able to infect. Specificity is usually mediated by the tail fibers of bacteriophages, that are involved in the interaction with receptors expressed on cells. A bacteriophage "specific" for E. coli more preferably designates a bacteriophage which can infect one or several E. coli strains and which cannot infect non-E. coli bacteria under physiological conditions.

As used herein, the term "polypeptide" refers to polypeptides of any size, including small peptides of e.g., from 5 to 20 amino acids, longer polypeptides, proteins or fragments thereof.

The term "PLE" or "Productive Lytic Effect" designates the ratio between burst size and productive lytic time of a given bacteriophage. Burst size and productive lytic time are parameters defining phage-host interaction and correspond, respectively, to the mean yield of bacteriophage particles produced by infection of one bacterium by one phage, and to the time taken by a free bacteriophage to lyse a bacterial cell.

In the context of the present specification, the term "isolated bacteriophage" should be considered to mean material removed from its original environment in which it naturally occurs. In relation to a bacteriophage, the term designates, particularly a phage that is e.g., cultivated, purified and/or cultured separately from the environment in which it is naturally located. In relation to a nucleic acid or polypeptide, the term "isolated" designates e.g., a nucleic acid molecule or polypeptide which is separated from at least some of the components of its natural environment such as, e.g., a protein, lipid, and/or nucleic acid.

The terms "pharmaceutically or veterinary acceptable" as used herein refers to any material (e.g., carrier, excipient or vehicle) that is compatible for use in a mammalian subject. Such includes physiologically acceptable solutions or vehicles that are harmless or do not cause any significant specific or non-specific immune reaction to an organism or do not abrogate the biological activity of the active compound. For formulation of the composition into a liquid preparation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If necessary, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations.

As used herein, "PFU" means plaque forming unit, as it is well defined in the art. Lytic bacteriophages lyse the host cell, causing a zone of clearing (or plaque) on a culture plate. Theoretically, each plaque is formed by one phage and the number of plaques multiplied by the dilution factor is equal to the total number of phages in a test preparation.

The term "treatment" or "therapy" designates both a curative treatment and/or a prophylactic treatment of a disease. A curative treatment is defined as a treatment resulting in cure or a treatment alleviating, improving and/or eliminating, reducing and/or stabilizing the symptoms of a disease or the suffering that it causes directly or indirectly. A prophylactic treatment comprises both a treatment resulting in the prevention of a disease and a treatment reducing and/or delaying the incidence of a disease or the risk of its occurrence.

The term "mammal" includes human subjects as well as non-human mammals such as pets (e.g., dogs, cats), horses, ruminants, sheep, goats, pigs, etc.

The term "biofilm" as used herein designates to be a heterogeneous bacterial formation growing on various surfaces; preferably a bacterial community growing embedded in an exopolysaccharide matrix adhered onto solid biological or non-biological surfaces.

The term "compromise" as used herein refers to any alteration of the integrity. By compromising a bacterial biofilm, it is understood a penetration of the biofilm by bacteriophage, an infection of biofilm-associated bacteria and/or a lysis thereof and/or a partial or an entire clearing of the biofilm (i.e. by stopping colonization and/or disrupting biofilms).

The term "sample", as used herein, means any sample containing cells. Examples of such samples include fluids such as blood, plasma, saliva, or urine as well as biopsies, organs, tissues or cell samples. The sample may be treated prior to its use.

As used herein, the term "subject" or "patient" refers to an animal, preferably to a mammal, even more preferably to a human, including adult and child. However, the term "subject" also encompasses non-human animals, in particular mammals such as dogs, cats, horses, cows, pigs, sheep and non-human primates, among others.

The term "efficacy" of treatment or "response" to a bacteriophage therapy as used herein refers to a treatment which results in a decrease in the number of *E. coli* strains in a subject after bacteriophage treatment when compared to the number of *E. coli* strains before treatment. A "good responder" subject refers to a subject who shows or will show a clinically significant recovery when treated with a bacteriophage therapy.

The term "Cocktail" or composition of bacteriophages designates a combination of two or more different bacteriophages. The bacteriophages in a cocktail/composition are preferably formulated together, i.e., in a same vessel or packaging, although they may be used as kits of parts wherein the (or some of the) bacteriophages are formulated or packaged separately and combined when used or administered.

DESCRIPTION OF EMBODIMENTS

The present invention is related to novel bacteriophage therapies. More particularly, the present invention relates to novel bacteriophages having a high specificity against *Escherichia coli* strains, their manufacture, components thereof, compositions comprising the same and the uses thereof in phage therapy.

Bacteriophages:

In a first aspect, the invention discloses the isolation and characterization of novel bacteriophages that are specific for *E. coli* strains and present, either alone or in combination(s), remarkable host range spectrum of lytic activity. These bacteriophages have been selected from environmental samples, isolated, and characterized. As indicated, the bacteriophages are, individually and in combination(s), active against *E. coli* strains. They are remarkable effective against pathogenic *E. coli* strains, such as antibiotic-resistant *E. coli* strains. Furthermore, bacteriophages of the invention have a remarkable productive lytic effect ("PLE") below 15, more preferably below 10 and still more preferably between 0.1 and 10. Furthermore, the bacteriophages of the invention are specific for *E. coli* strains, i.e., they do not causes lysis of non-*E. coli* bacteria. As will be illustrated further, the invention shows that these bacteriophages can be combined and formulated in conditions suitable for use as pharmaceutical or veterinary agents to exhibit targeted and very potent antibacterial effect against a controlled spectrum of *E. coli* strains.

More specifically, the following bacteriophages have been selected and characterized. Their corresponding nucleic acid sequences are also indicated.

TABLE 1

| SEQ ID number | Bacteriophage |
|---|---|
| SEQ ID NO: 1 | BP539 |
| SEQ ID NO: 2 | BP700 |
| SEQ ID NO: 3 | BP753 |
| SEQ ID NO: 4 | BP814 |
| SEQ ID NO: 5 | BP953 |
| SEQ ID NO: 6 | BP954 |
| SEQ ID NO: 7 | BP970 |
| SEQ ID NO: 8 | BP1002 |
| SEQ ID NO: 9 | BP1151 |
| SEQ ID NO: 10 | BP1155 |
| SEQ ID NO: 11 | BP1168 |
| SEQ ID NO: 12 | BP1176 |
| SEQ ID NO: 13 | BP1197 |

TABLE 1-continued

| SEQ ID number | Bacteriophage |
|---|---|
| SEQ ID NO: 14 | BP1226 |
| SEQ ID NO: 15 | BP1229 |

The lytic profile of these bacteriophages has been determined on a broad number of *E. coli* strains. These bacteriophages have been selected for their potency and combination potential, as disclosed in the following table. In this table, the lytic effect of the bacteriophages on reference and pathogen-resistant strains are presented, to confirm the high lytic potential.

The bacteriophages of the invention can be prepared by standard culture, isolation and purification methods. For example, *E. coli* producing bacteria are cultured, infected by a sample of a bacteriophage, and then treated to remove bacterial cells and debris. The enriched bacteriophage solution can be plated in a medium, for example agar medium, with embedded susceptible host strains of *E. coli* to obtain plaques. Then, single plaque can be picked out for subsequent bacteriophage purification and amplification. One or more cycles of selective amplification of bacteriophages of the invention may be performed, for example by mixing bacteriophages with the competent *E. coli*, followed by addition of a growth medium and incubation at selected test

TABLE 2

| Phage EC | 539 | 700 | 753 | 814 | 953 | 954 | 970 | 1002 | 1151 | 1155 | 1168 | 1176 | 1197 | 1226 | 1229 | 15 phages |
|---|---|---|---|---|---|---|---|---|---|---|---|---|---|---|---|---|
| 1 K12/DH5 | + | | | | + | | +* | | + | + | + | | +* | + | +* | + |
| 2 ECOR1 | | | | | + | | + | | | | | | | | | + |
| 3 ECOR2 | | | | | | | + | | +/− | + | | + | +/− | +/− | + | + |
| 4 ECOR4 | | | | | + | | | | | | | + | | | | + |
| 5 ECOR5 | | | | | + | | + | | | | | | | | | + |
| 6 ECOR10 | | + | | | | | +/− | | | | | | | | | + |
| 7 ECOR13 | | | | | + | | + | | + | +/− | +/− | + | + | + | +/− | + |
| 8 ECOR15 | + | | | | | | + | +/− | + | + | + | + | | | + | + |
| 9 ECOR24 | | | | | | + | | +/− | + | | | + | | | | + |
| 10 ECOR28 | | | | | + | | + | | | + | + | +/− | + | +/− | +/− | + |
| 11 ECOR35 | + | | | | +* | | | + | +/− | | + | +/− | | | | + |
| 12 ECOR38 | + | | | | | | + | | + | +/− | | | | | | + |
| 13 ECOR40 | + | | | | | | + | | + | +/− | | | | | | + |
| 14 ECOR46 | | + | | + | | | + | | | + | + | | + | | + | + |
| 15 ECOR48 | | + | | | | | +/− | | + | | | | + | +/− | + | + |
| 16 ECOR50 | | + | | + | | | | | +/− | +/− | +/− | | +/− | | +/− | + |
| 17 ECOR54 | +* | | | | | | | + | + | + | + | | + | | + | + |
| 18 ECOR55 | | +* | | +* | +* | | + | | | + | + | + | | | + | + |
| 19 ECOR56 | | +* | | + | | | +* | +* | | | | +/− | | | | + |
| 20 ECOR59 | | | | + | | | + | +/− | +* | +* | +/− | + | +* | + | | + |
| 21 ECOR60 | | + | | + | | | + | +/− | | | | +* | + | +/− | | + |
| 22 ECOR62 | + | | | | | + | | + | | | | | | | | + |
| 23 ECOR64 | + | + | | + | | | + | + | | | | | | | | + |
| 24 ECOR71 | + | | | | | | +/− | | + | +/− | | | + | | | + |
| 25 ECOR72 | | | | | + | | + | | | +/− | | +/− | +/− | +/− | +/− | + |

Boxes with an asterisk ("*") are examples of producing *E. coli* strains.

As can be seen from table 2, the phages have individually very strong lytic power, and combinations (or cocktails) of these bacteriophages may be produced that are able to kill all of the tested *E. coli* strains, thereby producing broad spectrum antibacterial compositions. As an illustration, a cocktail of all 15 phages of the invention is able to effectively kill all bacteria listed in Table 2.

Moreover, the specificity of the bacteriophages has been tested on many non-*E. coli* strains. More particularly, the experimental section demonstrates that the bacteriophages of the invention have no lytic effect on bacteria selected from *Pseudomonas aeruginosa*, *Acinebacter baumanii*, *Enterobacter aerogenes*, *Enterobacter asburiae*, *Enterobacter cloacae*, *Klebsiella pneumonia*, *Porteus mirabilis*, *Staphylococus aureus*, *Stenotrophomonas maltophila* and/or *Serratia marcescens*.

A particular object of the invention thus resides in a bacteriophage having lytic activity to an *E. coli* strain and having a genome comprising a nucleotide sequence selected from anyone of SEQ ID NOs: 1 to 15 or a sequence having at least 97% identity thereto, preferably at least 98% or 99% identity thereto.

A particular object of the invention thus resides in a bacteriophage having lytic activity to an *E. coli* strain and having a genome having or consisting of a nucleotide sequence selected from anyone of SEQ ID NOs: 1 to 15.

growing conditions. Following centrifugation, the cleared amplified supernatant is filtered through filter and subjected to another cycle of selective amplification or tested for presence of lytic activity. The titer of phage in a suspension and the visualization of plaque morphology of bacteriophages of the invention can be estimated by known methods, for example by plaque counting. Additionally, processing bacteriophages of the invention in various form (liquid, lyophilized, etc.) for short-, long-, freeze- or any other kind of storage can be carried out by any suitable method as it is well-known in the art (see Clark, 1962).

The activity of the bacteriophages of the invention can be assessed by methods well-known in the art, such as plaque assay also known as double agar method, based on the growing of bacteriophage with potential host bacteria and followed by assessing their ability to kill the host bacterial cell. In the plaque assay method, the bacteriophage induces lysis of target *E. coli* strains after a period of incubation in soft agar medium, resulting in zones of clearing on the plate known as plaques. In a preferred aspect, the bacteriophages of the invention exhibit, either alone or in combination, lytic activity to a pathogenic *E. coli* strain, including to an antibiotic-resistant *E. coli* strain, such as an ESBL *E. coli* strain. Furthermore, variants of these bacteriophages retaining a phenotypic (e.g., specificity and lytic activity) of these bacteriophages can be produced and/or isolated by techniques known per se in the art.

In a particular embodiment, the invention is related to BP539 bacteriophage, or any variant thereof. BP539 bacteriophage, or any variant thereof, can be produced or expanded in e.g., *E. coli* strain ECOR54. BP539, or any variant thereof, is specific and has lytic activity against K12/DH5, ECOR15, ECOR35, ECOR38, ECOR40, ECOR54, ECOR62, ECOR64 and/or ECOR71 strains. BP539 comprises a genome comprising a sequence as set forth in SEQ ID NO: 1 or having at least 80% identity, more preferably at least 85% identity, and still more preferably 90%, 92%, 94%, 95%, 96%, 97%, 98% or 99% identity to SEQ ID NO: 1. It is also provided an isolated nucleic acid sequence from BP539 bacteriophage, or variant thereof. The invention also encompasses isolated polypeptides encoded by BP539 bacteriophage, or variant thereof, or encoded by an isolated nucleic acid sequence from a BP539 bacteriophage of the invention.

BP539 bacteriophage of the invention is also characterized by a PLE below 15, more preferably below 10 and still more preferably of around 0.1.

In another particular embodiment, the invention is related to BP700 bacteriophage, or any variant thereof. BP700 bacteriophage, or any variant thereof, can be produced or expanded in e.g., *E. coli* strain ECOR55. BP700, or any variant thereof, is specific and has lytic activity against ECOR46, ECOR55, ECOR60 and/or ECOR64 strains. BP700 comprises a genome comprising a sequence as set forth in SEQ ID NO: 2 or having at least 80% identity, more preferably at least 85% identity, and still more preferably 90%, 92%, 94%, 95%, 96%, 97%, 98% or 99% identity to SEQ ID NO: 2. It is also provided an isolated nucleic acid sequence from BP700 bacteriophage, or variant thereof. The invention also encompasses isolated polypeptides encoded by BP700 bacteriophage, or variant thereof, or encoded by an isolated nucleic acid sequence from BP700 bacteriophage of the invention.

BP700 bacteriophage of the invention is also characterized by a PLE below 15, more preferably below 10 and still more preferably of around 2.

In still another aspect, the invention is related to BP753 bacteriophage, or any variant thereof. BP753 bacteriophage, or any variant thereof, can be produced or expanded in e.g., *E. coli* strain ECOR56. BP753, or any variant thereof, is specific and has lytic activity against ECOR10, ECOR48 and/or ECOR56 strains. BP753 comprises a genome comprising a sequence as set forth in SEQ ID NO: 3 or having at least 80% identity, more preferably at least 85% identity, and still more preferably 90%, 92%, 94%, 95%, 96%, 97%, 98% or 99% identity to SEQ ID NO: 3. It is also provided an isolated nucleic acid sequence from BP753 bacteriophage, or variant thereof. The invention also encompasses isolated polypeptides encoded by BP753 bacteriophage, or variant thereof, or encoded by an isolated nucleic acid sequence from BP753 bacteriophage of the invention.

BP753 bacteriophage of the invention is also characterized by a PLE below 15, more preferably below 10 and still more preferably of around 2.

In another aspect, the invention is related to BP814 bacteriophage, or any variant thereof. BP814 bacteriophage, or any variant thereof, can be produced or expanded in e.g., *E. coli* strain ECOR55. BP814, or any variant thereof, is specific and has lytic activity against ECOR46, ECOR50, ECOR55 and/or ECOR64 strains. BP814 comprises a genome comprising a sequence as set forth in SEQ ID NO: 4 or having at least 80% identity, more preferably at least 85% identity, and still more preferably 90%, 92%, 94%, 95%, 96%, 97%, 98% or 99% identity to SEQ ID NO: 4. It is also provided an isolated nucleic acid sequence from BP814 bacteriophage, or variant thereof. The invention also encompasses isolated polypeptides encoded by BP814 bacteriophage, or variant thereof, or encoded by an isolated nucleic acid sequence from BP814 bacteriophage of the invention.

BP814 bacteriophage of the invention is also characterized by a PLE below 15, more preferably below 10 and still more preferably of around 0.3.

In another particular embodiment, the invention is related to BP953 bacteriophage, or any variant thereof. BP953 bacteriophage, or any variant thereof, can be produced or expanded in e.g., *E. coli* strain ECOR55. BP953, or any variant thereof, is specific and has lytic activity against K12/DH5, ECOR1, ECOR46, ECOR50, ECOR54, ECOR55, ECOR59 and/or ECOR60 strains. BP953 comprises a genome comprising a sequence as set forth in SEQ ID NO: 5 or having at least 80% identity, more preferably at least 85% identity, and still more preferably 90%, 92%, 94%, 95%, 96%, 97%, 98% or 99% identity to SEQ ID NO: 5. It is also provided an isolated nucleic acid sequence from BP953 bacteriophage, or variant thereof. The invention also encompasses isolated polypeptides encoded by BP953 bacteriophage, or variant thereof, or encoded by an isolated nucleic acid sequence from BP953 bacteriophage of the invention.

BP953 bacteriophage of the invention is also characterized by a PLE below 15, more preferably below 10 and still more preferably of around 3.

In another particular embodiment, the invention is related to BP954 bacteriophage, or any variant thereof. BP954 bacteriophage, or any variant thereof, can be produced or expanded in e.g., *E. coli* strain ECOR35. BP954, or any variant thereof, is specific and has lytic activity against ECOR24, ECOR35, ECOR38, ECOR40, ECOR46 and/or ECOR62 strains. BP954 comprises a genome comprising a sequence as set forth in SEQ ID NO: 6 or having at least 80% identity, more preferably at least 85% identity, and still more preferably 90%, 92%, 94%. 95%. 96%. 97%. 98% or 99% identity to SEQ ID NO: 6. It is also provided an isolated nucleic acid sequence from BP954 bacteriophage, or variant thereof. The invention also encompasses isolated polypeptides encoded by BP954 bacteriophage, or variant thereof, or encoded by an isolated nucleic acid sequence from BP954 bacteriophage of the invention.

BP954 bacteriophage of the invention is also characterized by a PLE below 15, more preferably below 10 and still more preferably of around 3.

In still another aspect, the invention is related to BP970 bacteriophage, or any variant thereof. BP970 bacteriophage, or any variant thereof, can be produced or expanded in e.g., *E. coli* strain K12/DH5. BP970, or any variant thereof, is specific and has lytic activity against K12/DH5, ECOR1, ECOR2, ECOR5, ECOR10, ECOR13, ECOR15, ECOR28 and/or ECOR72 strains. BP970 comprises a genome comprising a sequence as set forth in SEQ ID NO: 7 or having at least 80% identity, more preferably at least 85% identity, and still more preferably 90%, 92%, 94%, 95%, 96%, 97%, 98% or 99% identity to SEQ ID NO: 7. It is also provided an isolated nucleic acid sequence from BP970 bacteriophage, or variant thereof. The invention also encompasses isolated polypeptides encoded by BP970 bacteriophage, or variant thereof, or encoded by an isolated nucleic acid sequence from BP970 bacteriophage of the invention.

BP970 bacteriophage of the invention is also characterized by a PLE below 15, more preferably below 10 and still more preferably of around 5.

In another particular embodiment, the invention is related to BP1002 bacteriophage, or any variant thereof. BP1002 bacteriophage, or any variant thereof, can be produced or expanded in e.g., *E. coli* strain ECOR56. BP1002, or any variant thereof, is specific and has lytic activity against ECOR15, ECOR24, ECOR35, ECOR38, ECOR40, ECOR48, ECOR54, ECOR55, ECOR56, ECOR59, ECOR60 and/or ECOR64 strains. BP1002 comprises a genome comprising a sequence as set forth in SEQ ID NO: 8 or having at least 80% identity, more preferably at least 85% identity, and still more preferably 90%, 92%, 94%, 95%, 96%, 97%, 98% or 99% identity to SEQ ID NO: 8. It is also provided an isolated nucleic acid sequence from BP1002 bacteriophage, or variant thereof. The invention also encompasses isolated polypeptides encoded by BP1002 bacteriophage, or variant thereof, or encoded by an isolated nucleic acid sequence from BP1002 bacteriophage of the invention.

BP1002 bacteriophage of the invention is also characterized by a PLE below 15, more preferably below 10 and still more preferably of around 5.

In another particular embodiment, the invention is related to BP1151 bacteriophage, or any variant thereof. BP1151 bacteriophage, or any variant thereof, can be produced or expanded in e.g., *E. coli* strain ECOR56. BP1151, or any variant thereof, is specific and has lytic activity against K12/DH5, ECOR2, ECOR13, ECOR15, ECOR24, ECOR35, ECOR38, ECOR40, ECOR46, ECOR48, ECOR50, ECOR54, ECOR56, ECOR59, ECOR60, ECOR62, ECOR64 and/or ECOR71 strains. BP1151 comprises a genome comprising a sequence as set forth in SEQ ID NO: 9 or having at least 80% identity, more preferably at least 85% identity, and still more preferably 90%, 92%, 94%, 95%, 96%, 97%, 98% or 99% identity to SEQ ID NO: 9. It is also provided an isolated nucleic acid sequence from BP1151 bacteriophage, or variant thereof. The invention also encompasses isolated polypeptides encoded by BP1151 bacteriophage, or variant thereof, or encoded by an isolated nucleic acid sequence from BP1151 bacteriophage of the invention.

BP1151 bacteriophage of the invention is also characterized by a PLE below 15, more preferably below 10 and still more preferably of around 10.

In another aspect, the invention is related to BP1155 bacteriophage, or any variant thereof. BP1155 bacteriophage, or any variant thereof, can be produced or expanded in e.g., *E. coli* strain ECOR59. BP1155, or any variant thereof, is specific and has lytic activity against K12/DH5, ECOR2, ECOR13, ECOR15, ECOR28, ECOR46, ECOR50, ECOR54, ECOR55, ECOR59 and/or ECOR71 strains. BP1155 comprises a genome comprising a sequence as set forth in SEQ ID NO: 10 or having at least 80% identity, more preferably at least 85% identity, and still more preferably 90%, 92%, 94%, 95%, 96%, 97%, 98% or 99% identity to SEQ ID NO: 10. It is also provided an isolated nucleic acid sequence from BP1155 bacteriophage, or variant thereof. The invention also encompasses isolated polypeptides encoded by BP1155 bacteriophage, or variant thereof, or encoded by an isolated nucleic acid sequence from BP1155 bacteriophage of the invention.

BP1155 bacteriophage of the invention is also characterized by a PLE below 15, more preferably below 10 and still more preferably of around 0.5.

In still another aspect, the invention is related to BP1168 bacteriophage, or any variant thereof. BP1168 bacteriophage, or any variant thereof, can be produced or expanded in e.g., *E. coli* strain ECOR59. BP1168, or any variant thereof, is specific and has lytic activity against K12/DH5, ECOR13, ECOR15, ECOR28, ECOR35, ECOR46, ECOR50, ECOR54, ECOR55, ECOR59, ECOR71 and/or ECOR72 strains. BP1168 comprises a genome comprising a sequence as set forth in SEQ ID NO: 11 or having at least 80% identity, more preferably at least 85% identity, and still more preferably 90%, 92%, 94%, 95%, 96%, 97%, 98% or 99% identity to SEQ ID NO: 11. It is also provided an isolated nucleic acid sequence from BP1168 bacteriophage, or variant thereof. The invention also encompasses isolated polypeptides encoded by BP1168 bacteriophage, or variant thereof, or encoded by an isolated nucleic acid sequence from BP1168 bacteriophage of the invention.

BP1168 bacteriophage of the invention is also characterized by a PLE below 15, more preferably below 10 and still more preferably of around 0.8.

In another aspect, the invention is related to BP1176 bacteriophage, or any variant thereof. BP1176 bacteriophage, or any variant thereof, can be produced or expanded in e.g., *E. coli* strain ECOR60. BP1176, or any variant thereof, is specific and has lytic activity against K12/DH5, ECOR2, ECOR4, ECOR13, ECOR15, ECOR24, ECOR28, ECOR35, ECOR55, ECOR56, ECOR59 and/or ECOR60 strains. BP1176 comprises a genome comprising a sequence as set forth in SEQ ID NO: 12 or having at least 80% identity, more preferably at least 85% identity, and still more preferably 90%, 92%, 94%, 95%, 96%, 97%, 98% or 99% identity to SEQ ID NO: 12. It is also provided an isolated nucleic acid sequence from BP1176 bacteriophage, or variant thereof. The invention also encompasses isolated polypeptides encoded by BP1176 bacteriophage, or variant thereof, or encoded by an isolated nucleic acid sequence from BP1176 bacteriophage of the invention.

BP1176 bacteriophage of the invention is also characterized by a PLE below 15, more preferably below 10 and still more preferably of around 4.

In still another aspect, the invention is related to BP1197 bacteriophage, or any variant thereof. BP1197 bacteriophage, or any variant thereof, can be produced or expanded in e.g., *E. coli* strain K12/DH5. BP1197, or any variant thereof, is specific and has lytic activity against K12/DH5, ECOR2, ECOR13, ECOR15, ECOR28, ECOR46, ECOR48, ECOR50, ECOR54, ECOR59, ECOR60, ECOR71 and/or ECOR72 strains. BP1197 comprises a genome comprising a sequence as set forth in SEQ ID NO: 13 or having at least 80% identity, more preferably at least 85% identity, and still more preferably 90%, 92%, 94%, 95%, 96%, 97%, 98% or 99% identity to SEQ ID NO: 13. It is also provided an isolated nucleic acid sequence from BP1197 bacteriophage, or variant thereof. The invention also encompasses isolated polypeptides encoded by BP1197 bacteriophage, or variant thereof, or encoded by an isolated nucleic acid sequence from BP1197 bacteriophage of the invention.

BP1197 bacteriophage of the invention is also characterized by a PLE below 15, more preferably below 10 and still more preferably of around 1.

In an aspect, the invention is related to BP1226 bacteriophage, or any variant thereof. BP1226 bacteriophage, or any variant thereof, can be produced or expanded in e.g., *E. coli* strain ECOR59. BP1226, or any variant thereof, is specific and has lytic activity against K12/DH5, ECOR2, ECOR13, ECOR28, ECOR48, ECOR59, ECOR60 and/or ECOR72 strains. BP1226 comprises a genome comprising a sequence as set forth in SEQ ID NO: 14 or having at least 80% identity, more preferably at least 85% identity, and still more preferably 90%, 92%, 94%, 95%, 96%, 97%, 98% or 99% identity to SEQ ID NO: 14. It is also provided an isolated nucleic acid sequence from BP1226 bacteriophage, or variant thereof. The invention also encompasses isolated polypeptides encoded by BP1226 bacteriophage, or variant thereof, or encoded by an isolated nucleic acid sequence from BP1226 bacteriophage of the invention.

BP1226 bacteriophage of the invention is also characterized by a PLE below 15, more preferably below 10 and still more preferably of around 5.

In another particular embodiment, the invention is related to BP1229 bacteriophage, or any variant thereof. BP1229 bacteriophage, or any variant thereof, can be produced or expanded in e.g., *E. coli* strain K12/DH5. BP1229, or any variant thereof, is specific and has lytic activity against K12/DH5, ECOR2, ECOR13, ECOR15, ECOR28, ECOR46, ECOR48, ECOR50, ECOR54, ECOR55, ECOR59, and/or ECOR72 strains. BP1229 comprises a genome comprising a sequence as set forth in SEQ ID NO: 15 or having at least 80% identity, more preferably at least 85% identity, and still more preferably 90%, 92%, 94%, 95%, 96%, 97%, 98% or 99% identity to SEQ ID NO: 15. It is also provided an isolated nucleic acid sequence from BP1229 bacteriophage, or variant thereof. The invention also encompasses isolated polypeptides encoded by BP1229 bacteriophage, or variant thereof, or encoded by an isolated nucleic acid sequence from BP1229 bacteriophage of the invention.

BP1229 bacteriophage of the invention is also characterized by a PLE below 15, more preferably below 10 and still more preferably of around 6.

Nucleic Acids and Polypeptides

The invention also relates to a nucleic acid contained in a bacteriophage of the invention, or any fragment of such a nucleic acid. The term fragment designates, more preferably, a fragment containing (or consisting of) an open reading frame. The nucleic acid may be DNA or RNA, single- or double-stranded.

The nucleic acid can be isolated from the deposited bacteriophages, or produced using recombinant DNA technology (e.g., polymerase chain reaction (PCR) amplification, cloning), enzymatic or chemical synthesis, or combinations thereof, according to general techniques known per se in the art. Also included are homologous sequences and fragments thereof including, but not limited to, natural allelic variants and modified nucleic acid sequences in which nucleotides have been inserted, deleted, substituted, and/or inverted.

In a particular embodiment, the invention relates to a nucleic acid comprising a sequence selected from anyone of SEQ ID NOs: 1-15, or a sequence having at least 90%, 92%, 94%, 95%, 96%, 97%, 98%, 99% or more sequence identity to anyone of SEQ ID NOs: 1-15.

In another particular embodiment, the invention relates to a nucleic acid comprising the sequence of a fragment of a sequence selected from anyone of SEQ ID NOs: 1-15, or a fragment of a sequence having at least 90%, 92%, 94%, 95%, 96%, 97%, 98%, 99% or more sequence identity to anyone of SEQ ID NOs: 1-15, said fragment comprising an open reading frame or a regulatory element such as a promoter.

In a particular embodiment, the invention relates to a nucleic acid having or consisting of a sequence selected from anyone of SEQ ID NOs: 1-15, or a sequence having at least 90%, 92%, 94%, 95%, 96%, 97%, 98%, 99% or more sequence identity to anyone of SEQ ID NOs: 1-15.

The nucleic acid of the invention can be in free form, or cloned in a vector.

In a further aspect, the invention also relates to an isolated polypeptide encoded by a nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15. The polypeptides may be produced by techniques known per se in the art such as synthesis, recombinant technology, or combinations thereof. The polypeptides may be isolated or purified, and used as antibacterial agents or as reagents for in vitro analyses.

Compositions of the Invention:

One aspect of the invention relates to compositions comprising at least one bacteriophage as described above, more preferably at least 2 or more and, optionally, a pharmaceutically or veterinary acceptable excipient. As described, the bacteriophages of the invention have very potent lytic activity against *E. coli* strains. Combinations of these bacteriophages may be produced to expand the host spectrum and produce highly effective antibacterial compositions.

More particularly, the invention relates to an antibacterial composition comprising at least two bacteriophages having lytic activity against an *E. coli* strain, said at least two bacteriophages being selected from the bacteriophages having a genome comprising a nucleotide sequence of anyone of SEQ ID NOs: 1 to 15 or a sequence having at least 90% identity thereto, preferably at least 91%, 92%, 93%, 94%, 95%, 96%, 97%, 98% or 99% identity thereto.

In a preferred embodiment, the compositions of the invention comprise at least three, even more preferably at least four distinct bacteriophages selected from the bacteriophages having a genome comprising a nucleotide sequence of anyone of SEQ ID NOs: 1 to 15 or a sequence having at least 90% identity thereto, preferably at least 91%, 92%, 93%, 94%, 95%, 96%, 97%, 98% or 99% identity thereto. Compositions of the invention may comprise at least 5, 6, 7, 8, 9, 10, 11, 11, 12, 13, 14 or all of the 15 distinct bacteriophages as disclosed above.

One aspect of the invention is related to a composition at least one bacteriophage selected from BP539, BP700, BP753, BP814, BP953, BP954, BP970, BP1002, BP1151, BP1155, BP1168, BP1176, BP1197, BP1226, and/or BP1229, and variants thereof.

The invention also concerns a composition comprising at least two distinct bacteriophages selected from BP539, BP700, BP753, BP814, BP953, BP954, BP970, BP1002, BP1151, BP1155, BP1168, BP1176, BP1197, BP1226, and/or BP1229, and variants thereof.

Preferably, a composition of the invention comprises at least three distinct bacteriophages, more preferably at least four distinct bacteriophages, still more preferably at least five distinct bacteriophages, still more preferably at least six distinct bacteriophages, more preferably at least seven distinct bacteriophages, more preferably at least eight distinct bacteriophages, still more preferably at least nine distinct bacteriophages and still more preferably at least ten distinct bacteriophages selected from BP539, BP700, BP753, BP814, BP953, BP954, BP970, BP1002, BP1151, BP1155, BP1168, BP1176, BP1197, BP1226, and/or BP1229, and variants thereof.

In a particular embodiment, a composition of the invention comprises BP539 in combination with at least one further bacteriophage selected from BP700, BP753, BP814, BP1151, BP1176, and BP1168.

In another particular embodiment, a composition of the invention comprises BP1002 in combination with at least one further bacteriophage selected from BP1151, BP1155, BP1168, BP1176 and BP1197.

In another particular embodiment, the composition comprises BP1155 in combination with at least one further bacteriophage selected from BP1168, BP1197, BP1226, BP1229 and BP1176.

In another preferred embodiment, the composition comprises BP1151 in combination with at least one further bacteriophage selected from BP1176, BP953, BP970, BP700 and BP1002.

In another preferred embodiment, the composition comprises BP953 and/or BP1168 and/or BP1176, optionally in further combination with at least one further bacteriophage of the invention.

The invention particularly relates to a composition comprising a combination of bacteriophages BP953+BP1168. Such a composition could kill 100% tested hemorrhagic *E. coli* strains and nearly 70% of the 25 *E. coli* bacteria of Table 2 (see Example 3.1).

The invention also relates to a composition comprising a combination of bacteriophages BP953+BP1168+BP1229. Such a composition can kill *E. coli* bacteria type O157, O144 and O104, including hemorrhagic strains (see Example 3.2).

The invention also relates to a composition comprising a combination of bacteriophages BP953+BP1151+BP1155+BP1176. Such a composition could kill 80% of all tested *E. coli* bacteria isolated from hospitals (see Example 3.3).

The invention also relates to a composition comprising a combination of bacteriophages BP700+BP953+BP970+BP1002+BP1176. Such a composition could kill 100% of tested ST131-type *E. coli* bacteria, at least 80% of tested BLSE *E. coli* bacteria and at least 93% of tested BMR-type *E. coli* bacteria (see Example 3.4).

The invention also relates to a composition comprising a combination of bacteriophages BP1002+BP1151+BP1155+BP1168+BP1176. Such a composition can kill 100% of tested meningitis-causing *E. coli* bacteria (see Example 3.5).

The invention also relates to a composition comprising a combination of bacteriophages BP539+BP700+BP753+BP814+BP1151+BP1176+BP1168. Such a composition could kill nearly 96% of the 24 *E. coli* bacteria of the ECOR collection of Table 2 (see Example 3.6).

The invention also relates to a composition comprising a combination of all of the bacteriophages BP539, BP700, BP753, BP814, BP953, BP954, BP970, BP1002, BP1151, BP1155, BP1168, BP1176, BP1197, BP1226, and/or BP1229, or variants thereof. Such a composition could kill 100% of the 25 *E. coli* bacteria of Table 2 (see Example 3.7).

Specific examples of compositions of the invention comprise:

a bacteriophage having a genome comprising a nucleotide sequence of SEQ ID NO: 5 or a sequence having at least 90% identity thereto, and a bacteriophage having a genome comprising a nucleotide sequence of SEQ ID NO: 11 or a sequence having at least 90% identity thereto;

a bacteriophage having a genome comprising a nucleotide sequence of SEQ ID NO: 5 or a sequence having at least 90% identity thereto, and a bacteriophage having a genome comprising a nucleotide sequence of SEQ ID NO: 11 or a sequence having at least 90% identity thereto, and a bacteriophage having a genome comprising a nucleotide sequence of SEQ ID NO: 15 or a sequence having at least 90% identity thereto;

a bacteriophage having a genome comprising a nucleotide sequence of SEQ ID NO: 5 or a sequence having at least 90% identity thereto, and a bacteriophage having a genome comprising a nucleotide sequence of SEQ ID NO: 9 or a sequence having at least 90% identity thereto, and a bacteriophage having a genome comprising a nucleotide sequence of SEQ ID NO: 10 or a sequence having at least 90% identity thereto, and a bacteriophage having a genome comprising a nucleotide sequence of SEQ ID NO: 12 or a sequence having at least 90% identity thereto;

a bacteriophage having a genome comprising a nucleotide sequence of SEQ ID NO: 2 or a sequence having at least 90% identity thereto, and a bacteriophage having a genome comprising a nucleotide sequence of SEQ ID NO: 5 or a sequence having at least 90% identity thereto, and a bacteriophage having a genome comprising a nucleotide sequence of SEQ ID NO: 7 or a sequence having at least 90% identity thereto, and a bacteriophage having a genome comprising a nucleotide sequence of SEQ ID NO: 8 or a sequence having at least 90% identity thereto, and a bacteriophage having a genome comprising a nucleotide sequence of SEQ ID NO: 12 or a sequence having at least 90% identity thereto;

a bacteriophage having a genome comprising a nucleotide sequence of SEQ ID NO: 8 or a sequence having at least 90% identity thereto, and a bacteriophage having a genome comprising a nucleotide sequence of SEQ ID NO: 9 or a sequence having at least 90% identity thereto, and a bacteriophage having a genome comprising a nucleotide sequence of SEQ ID NO: 10 or a sequence having at least 90% identity thereto, and a bacteriophage having a genome comprising a nucleotide sequence of SEQ ID NO: 11 or a sequence having at least 90% identity thereto, and a bacteriophage having a genome comprising a nucleotide sequence of SEQ ID NO: 12 or a sequence having at least 90% identity thereto; or a bacteriophage having a genome comprising a nucleotide sequence of SEQ ID NO: 1 or a sequence having at least 90% identity thereto, and a bacteriophage having a genome comprising a nucleotide sequence of SEQ ID NO: 2 or a sequence having at least 90% identity thereto, and a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto, and a bacteriophage having a genome comprising a nucleotide sequence of SEQ ID NO: 9 or a sequence having at least 90% identity thereto, and a bacteriophage having a genome comprising a nucleotide sequence of SEQ ID NO: 12 or a sequence having at least 90% identity thereto, and a bacteriophage having a genome comprising a nucleotide sequence of SEQ ID NO: 11 or a sequence having at least 90% identity thereto.

A specific embodiment of the invention relates to a composition comprising:

a bacteriophages having a genome comprising a nucleotide sequence of SEQ ID NO: 1 or a sequence having at least 90% identity thereto;

a bacteriophages having a genome comprising a nucleotide sequence of SEQ ID NO: 2 or a sequence having at least 90% identity thereto;

a bacteriophages having a genome comprising a nucleotide sequence of SEQ ID NO: 3 or a sequence having at least 90% identity thereto;

a bacteriophages having a genome comprising a nucleotide sequence of SEQ ID NO: 4 or a sequence having at least 90% identity thereto;
a bacteriophages having a genome comprising a nucleotide sequence of SEQ ID NO: 5 or a sequence having at least 90% identity thereto;
a bacteriophages having a genome comprising a nucleotide sequence of SEQ ID NO: 6 or a sequence having at least 90% identity thereto;
a bacteriophages having a genome comprising a nucleotide sequence of SEQ ID NO: 7 or a sequence having at least 90% identity thereto;
a bacteriophages having a genome comprising a nucleotide sequence of SEQ ID NO: 8 or a sequence having at least 90% identity thereto;
a bacteriophages having a genome comprising a nucleotide sequence of SEQ ID NO: 9 or a sequence having at least 90% identity thereto;
a bacteriophages having a genome comprising a nucleotide sequence of SEQ ID NO: 10 or a sequence having at least 90% identity thereto;
a bacteriophages having a genome comprising a nucleotide sequence of SEQ ID NO: 11 or a sequence having at least 90% identity thereto;
a bacteriophages having a genome comprising a nucleotide sequence of SEQ ID NO: 12 or a sequence having at least 90% identity thereto;
a bacteriophages having a genome comprising a nucleotide sequence of SEQ ID NO: 13 or a sequence having at least 90% identity thereto;
a bacteriophages having a genome comprising a nucleotide sequence of SEQ ID NO: 14 or a sequence having at least 90% identity thereto; and
a bacteriophages having a genome comprising a nucleotide sequence of SEQ ID NO: 15 or a sequence having at least 90% identity thereto.

The compositions of the invention exert lytic activity towards bacterial pathogen *E. coli*. The compositions of the invention may further comprise additional antibacterial agents, particularly other bacteriophages having distinct host specificity.

Preferred compositions of the invention are lytic against antibiotic-resistant *E. coli* strains.

Further preferred compositions of the invention are lytic against more that 90% of all bacterial strains of the EcoR collection, a reference collection of *E. coli* strains found in nature.

The antibacterial compositions of the invention may be in various forms, such as liquid, semi-liquid, solid or lyophilized formulations.

It is desired in an aspect of the invention that the composition comprises between $10^{e2}$ and $10^{e12}$ PFU of at least one bacteriophage of the invention, preferably between $10^{e5}$ and $10^{e10}$ PFU. When the antibacterial composition comprises several bacteriophages as defined above, it is preferred that the composition comprises between $10^{e2}$ and $10^{e12}$ PFU of each present bacteriophage of the invention.

The compositions of the invention may comprise any effective amount of the selected bacteriophage(s). Preferably, they comprise between $10^{e2}$ and $10^{e12}$ PFU of each of said bacteriophages, preferably between $10^{e5}$ and $10^{e10}$ PFU. The relative amounts of each type of bacteriophage in a composition of the invention may be adjusted by a skilled artisan. Typically, when the antibacterial composition comprises several (n) distinct bacteriophages as defined above, the total relative amount % A of each bacteriophage in the composition is more preferably % $A=(100/n_t) \times V$, wherein $n_t$ represents the number of distinct types of bacteriophages and V is a variability factor comprised between 0.2 and 5. Most preferably, V is comprised between 0.3 and 3, even more preferably between 0.5 and 2, generally between 0.8 and 1.5. In a typical embodiment, when the antibacterial composition comprises several bacteriophages as defined above, it is preferred that the composition comprises between $10^{e2}$ and $10^{e12}$ PFU of each present bacteriophage of the invention. Preferably, each type of bacteriophage is present in a composition of the invention in approximately equal relative amounts.

The compositions of the invention preferably comprise a suitable diluent or carrier, such as a pharmaceutically or veterinary acceptable excipient or carrier. Compositions according to the present invention may include any excipient or carrier, such as thickeners, diluents, buffers, preservatives, surface active agents and the like, in addition to the bacteriophage(s) of choice. Such includes physiologically acceptable solutions or vehicles that are harmless or do not cause any significant specific or non-specific immune reaction to an organism or do not abrogate the biological activity of the bacteriophage. For liquid formulation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If appropriate, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations. Formulations for topical administration may include, band aids, dressings, patches, films, ointments, lotions, creams, gels, drops, suppositories, sprays, nebulizer, tampons, sanitary towels, liquids and powders. Formulations for decontamination or for medical use may also include aerosols or sprays.

The compositions of the invention may be used in the medical field, including the human or veterinary medical areas, for e.g. the treatment of an infection in a mammal or for improving a subject's condition.

The compositions may be used to kill *E. coli* bacteria in an organism, for treating an infection. The composition may also be used for improving the condition of a mammal by modifying the microbial flora in said mammal. In particular, the compositions of the invention can specifically remove *E. coli* strains on the skin or mucous membranes of a mammal, thus modifying its microbial flora and restoring a proper balance.

In a particular embodiment, the invention also relates to a method for treating an infection in a mammal comprising the administration to said mammal of a composition or bacteriophage or nucleic acid or polypeptide as defined above.

In a particular embodiment the method comprises administering at least one, preferably at least two, even more preferably at least three bacteriophages selected from BP539, BP700, BP753, BP814, BP953, BP954, BP970, BP1002, BP1151, BP1155, BP1168, BP1176, BP1197, BP1226, and/or BP1229, or variants thereof.

The invention also relates to the use of a composition, bacteriophage, nucleic acid or polypeptide as described for the manufacture of a medicament for treating an infection in a mammal, or for restoring microbial flora in said mammal.

The compositions or agents of the invention may be administered by any convenient route, including intravenous, oral, transdermal, subcutaneous, mucosal, intramuscular, intrapulmonary, intranasal, parenteral, rectal, vaginal and topical. In a preferred embodiment, the bacteriophages or compositions are administered by topical route, e.g., by application on the skin of a subject. The compositions may be administered directly or indirectly, e.g., via a support. In this regard, the compositions may, for example, be applied or sprayed to the afflicted area. Compositions of the invention can also be administered by oral or parenteral routes. The dosage suitable for applying, spraying, or administrating the compositions of the present invention can be adjusted by the skilled person depending on a variety of factors including formulation, mode of administration, age, weight, sex, condition, diet of the mammal being treated at the time of administration, route of administration and reaction sensitivity. A physician having ordinary skills in the art can readily determine and prescribe the effective amount of the composition required.

The dosing can also be adjusted by the skilled person so that a lytic activity against antibiotic-resistant *E. coli* strains is obtained. An efficient dose to obtain a lytic activity in vivo typically includes a concentration of at least $10^{e2}$ PFU/ml, preferably from about $10^{e2}$ to $10^{e12}$ PFU/ml, depending on the administration route. Administration may be performed only once or, if needed, repeated.

The compositions of the invention may be administered to treat *E. coli* infections, typically respiratory tract, urinary tract, burns, wounds, ear, skin and soft tissue, gastrointestinal or post-surgical infections.

As shown in the experimental section, the bacteriophages and compositions of the invention are able to selectively kill *E. coli* bacteria in vitro or in vivo. The compositions can destroy mixtures of different *E. coli* bacteria, even in vivo, even at low dosage. Furthermore, the compositions of the invention are effective in killing bacteria embedded in biofilms, which is particularly important for pathogenic bacteria. Also, the compositions and bacteriophages of the invention are strictly unable to affect mammalian cells, and are, therefore, specific and devoid of side effects in vivo.

The invention also relates to the use of a composition, bacteriophage, nucleic acid or polypeptide of the invention for decontaminating a material. Due to their potent antibacterial effect, and to their ability to even compromise the integrity of a bacterial biofilm, the compositions of the invention can be used as decontaminating agent, to eliminate or at least cause a reduction in bacterial numbers on a material. Such methods may be applied for the treatment of a variety of biological or non-biological surfaces in both medical and non-medical contexts, including solid materials or devices such as, for example, contact lenses, surfaces of devices to be implanted into the body, pipes, ducts, laboratory vessels, textiles, etc.

Diagnostic/Predictive Tests of the Invention:

The invention also concerns a method for predicting or determining the efficacy of a bacteriophage therapy in a subject, wherein the method comprises a step of determining a lytic activity of one or more bacteriophage selected from BP539, BP700, BP753, BP814, BP953, BP954, BP970, BP1002, BP1151, BP1155, BP1168, BP1176, BP1197, BP1226, and/or BP1229 to an *E. coli* strain from a sample from said subject, such a lytic activity being indicative of an efficient treatment. In a preferred aspect, the method further optionally comprises a step of treating said subject by one or more bacteriophages having a lytic activity to an *E. coli* strain from a sample of said subject.

In another aspect, the invention provides a method for selecting a subject or determining whether a subject is susceptible to benefit from a bacteriophage therapy, wherein the method comprises the step of determining a lytic activity of one or more bacteriophage selected from BP539, BP700, BP753, BP814, BP953, BP954, BP970, BP1002, BP1151, BP1155, BP1168, BP1176, BP1197, BP1226, and/or BP1229 to an *E. coli* strain from a sample of said subject, a lytic activity of one or more bacteriophage of the invention to at least one *E. coli* strain indicating a responder subject.

Another object of the invention relates to a method for predicting the response of a subject to a bacteriophage therapy, wherein the method comprises the step of determining a lytic activity of one or more bacteriophage selected from BP539, BP700, BP753, BP814, BP953, BP954, BP970, BP1002, BP1151, BP1155, BP1168, BP1176, BP1197, BP1226, and/or BP1229 to an *E. coli* strain from a sample of said subject, a lytic activity of one or more bacteriophage of the invention to at least one *E. coli* strain being indicative of a good response to said therapy.

Further aspects and advantages of the invention will be disclosed in the following experimental section, which is illustrative only.

Examples

Materials and Methods

Phage Isolation and Preparation

MDR *E. coli* bacteria were used for isolating and enriching each virulent bacteriophage from environmental water. Environmental samples and overnight culture of bacteria in Luria Bertani (LB) were mixed and incubated at 37° C. for 24 h with shaking to enrich specific bacteriophages. At the end of incubation, drops of chloroform were added to the culture. The culture was spun down at 11,000 g for 5 minutes to remove bacterial cells and debris. The supernatant was subjected to 0.2 m filter to remove the residual bacterial cells. The enriched phage solution was plated on LB agar medium with *E. coli* embedded. Plaques formed on the plates after 24 h incubation at 37° C. Single plaque was picked out for subsequent phage purification and amplification. The phage was then stored at 4° C. in a suspension in LB broth or physiological saline.

The titer of phage in a suspension was estimated by plaque counting (Postic, 1961). 10-fold dilutions of a suspension were delivered on a dried lawn of the propagating strain. The plates were read after overnight incubation. The plaque-counting method also permitted visualization of plaque morphology.

Host Range Determination.

The host ranges of bacteriophages were determined among a collection of 26 *E. coli* from the ECOR collection. $10^9$ bacterial cells were mixed with melted agar and this mixture was poured on solid agar to make double layer agar plates. After solidification, isolated bacteriophage stock solutions were spotted on each plate with different bacterium strain. After allowing 20 min for the spots to be absorbed, the plates were inverted and incubated for 24 h at 37° C. before the degree of lysis was recorded.

Electron Microscopy.

Electron micrographs of each phage were taken with a transmission electron microscope.

Sequencing, Analysis and Annotation of Phage Genomes.

To isolate phage DNA, phages were propagated as described above. Phage DNA was isolated by extraction with phenol:chloroform:isoamyl alcohol (25:24:1, V/V), ethanol precipitation and resolution in water. Whole genome sequencing was done and the BLAST algorithm was used to determine the similarity to described genes in the National Center for Biotechnology Information [NCBI] database. The genomes were scanned for potential open reading frames (ORFs).

Example 1: Bacteriophage-Host Characteristics and Kinetics

One-step growth experiments were carried out according to the previous descriptions to determine first the productive lytic time, adsorption rate, and then the phage burst size. To determine the adsorption rate samples were taken at different time intervals to analyze the free phage particles in the solutions. For productive time and phage burst size determination, *E. coli* bacteria were mixed with phages solutions and phages were allowed to adsorb for 15 m. The mixture was subjected to centrifugation immediately at 5000 rpm for 10 min to remove free phage particles. The pellet was resuspended in 5 fresh LB medium and the culture was continuously incubated at 37° C. Samples were taken at 3 min intervals and phage titre was determined. These results permitted to calculate the number of phages produced per bacteria (burst size), the productive time and the productive lytic effect (PLE), as shown in table 3 below.

TABLE 3

| Phage | Productive lytic time (min) | Adsorption rate (ml-1 min-1) | BURST SIZE (PFU per bacterium) | PLE (PFU per bacterium per min) |
|---|---|---|---|---|
| 539 | 70 | 9.83E–09 | 9 | 0.13 |
| 700 | 15 | 1.04E–08 | 32 | 2.13 |
| 753 | 60 | 3.00E–08 | 119 | 1.98 |
| 814 | 30 | 2.30E–08 | 9 | 0.30 |
| 953 | 20 | 2.05E–08 | 66 | 3.30 |
| 954 | 20 | 2.01E–08 | 66 | 3.30 |
| 970 | 10 | 2.24E–08 | 46 | 4.60 |
| 1002 | 10 | 8.40E–09 | 49 | 4.90 |

TABLE 3-continued

| Phage | Productive lytic time (min) | Adsorption rate (ml-1 min-1) | BURST SIZE (PFU per bacterium) | PLE (PFU per bacterium per min) |
|---|---|---|---|---|
| 1151 | 10 | 2.10E–08 | 99 | 9.90 |
| 1155 | 15 | 1.21E–08 | 7 | 0.47 |
| 1168 | 10 | 8.70E–09 | 8 | 0.80 |
| 1176 | 60 | 1.56E–08 | 232 | 3.87 |
| 1197 | 45 | 6.60E–09 | 49 | 1.09 |
| 1226 | 30 | 8.87E–09 | 149 | 4.97 |
| 1229 | 55 | 6.55E–09 | 332 | 6.04 |

These results show that all phages have potent viral production capacity and absorption rates. Most phages have a PLE below 5, which demonstrates a remarkable profile. Phage 539 is particularly effective in this regard. In addition, the different PLE and adsorption times permit to create cocktails with selected variability.

Example 2: Preparation of a Cocktail Composition

The following cocktail compositions are constituted, each comprising between $10^{-9}$ and $10^{-11}$ pfu of each bacteriophage:

TABLE 4

| Cocktail | Phages |
|---|---|
| I | BP953 + BP1168 |
| II | BP953 + BP1168 + BP1229 |
| III | BP953 + BP1151 + BP1155 + BP1176 |
| IV | BP700 + BP953 + BP970 + BP1002 + BP1176 |
| V | BP1002 + BP1151 + BP1155 + BP1168 + BP1176 |
| VI | BP539 + BP700 + BP753 + BP814 + BP1151 + BP1176 + BP1168 |

The following additional two cocktail compositions comprising all of the various phages are constituted, covering the most important diversity of *E. coli* species.

TABLE 5A cocktail composition A:

| Phage | BP539 | BP 700 | BP 753 | BP 814 | BP 953 | BP 954 | BP970 | BP1002 |
|---|---|---|---|---|---|---|---|---|
| Titer | $2.72^{E+09}$ | $8.00^{E+09}$ | $2.27^{E+08}$ | $5.89^{E+07}$ | $4.53^{E+10}$ | $3.00^{E+08}$ | $4.02^{E+08}$ | $9.73^{E+08}$ |

| Phage | BP1151 | BP1155 | BP1168 | BP1176 | BP1197 | BP1226 | B1229 |
|---|---|---|---|---|---|---|---|
| Titer | $1.56^{E+09}$ | $3.00^{E+10}$ | $7.77^{E+09}$ | $1.00^{E+10}$ | $3.91^{E+09}$ | $4.44^{E+06}$ | $9.11^{E+09}$ |

TABLE 5B cocktail composition B:

| Phage | BP539 | BP 700 | BP 753 | BP 814 | BP 953 | BP 954 | BP970 | BP1002 |
|---|---|---|---|---|---|---|---|---|
| Titer | $8.85^{E+08}$ | $1.89^{E+08}$ | $7.26^{E+07}$ | $3.04^{E+08}$ | $9.47^{E+08}$ | $3.89^{E+08}$ | $9.56^{E+07}$ | $2.09^{E+09}$ |

| Phage | BP1151 | BP1155 | BP1168 | BP1176 | BP1197 | BP1226 | B1229 |
|---|---|---|---|---|---|---|---|
| Titer | $7.35^{E+08}$ | $2.57^{E+09}$ | $3.01^{E+09}$ | $1.77^{E+09}$ | $1.03^{E+10}$ | $2.00^{E+09}$ | $1.56^{E+09}$ |

Example 3: Sensitivity of Bacteria to Bacteriophage Cocktails of the Invention

Various strains of bacteria were tested with a bacteriophage cocktail of the invention at $2.10^9$ bacteriophages/ml. Different bacterial concentrations were plated on the bacteriophage cocktail at $2.10^9$ bacteriophages/ml and incubated 24 h at 37° C.

Cocktails are tested on distinct *E. coli* bacteria listed in table 2 as well as additional *E. coli* bacteria, including meningitis-causing bacteria from R. Debre collection (37 strains), BLSE (5 strains) and ST131 (9 strains) type *E. coli* bacteria, *E. coli* bacteria derived from hospitalized patients (35 strains), and haemorrhagic *E. coli* bacteria of O157, O144 and O104 type (3 strains). The % of bacteria species sensitive to the cocktails are listed in table 6 below:

Example 3.1: Efficacy of Cocktail I

As shown in the following Table 6 below, cocktail I is able to destroy 100% of tested haemorrhagic *E. coli* bacteria.

TABLE 6

|  | BP953 | BP1168 | Cocktail I |
| --- | --- | --- | --- |
| O157:133 |  | + | + |
| O144:227 |  | + | + |
| O104:H4 | + |  | + |

Furthermore, cocktail I can also destroy nearly 70% of the 25 *E. coli* bacteria of table 2.

Example 3.2: Efficacy of Cocktail II

As shown in the following Table 7, cocktail II is able to destroy 100% of tested haemorrhagic *E. coli* bacteria.

TABLE 7

|  | BP953 | BP1168 | BP1229 | Cocktail II |
| --- | --- | --- | --- | --- |
| O157:133 |  | + | + | + |
| O144:227 |  | + | + | + |
| O104:H4 | + |  |  | + |

Furthermore, cocktail II can also destroy 76% of the 25 *E. coli* bacteria of table 2.

Example 3.3: Efficacy of Cocktail III

As shown in the following Table 8, cocktail III is able to destroy at least 80% of tested *E. coli* strains isolated from hospitalized patients.

TABLE 8

|  | BP953 | BP1151 | B1155 | BP1176 | Cocktail III |
| --- | --- | --- | --- | --- | --- |
| NDM-1 |  |  |  | + | + |
| SH1 | + |  |  | + | + |
| SH4 |  | + |  |  | + |
| SH5 |  | + |  | + | + |
| SH7 |  | + |  | +/− | + |
| SH9 |  | + |  | + | + |
| SH11 |  |  |  |  |  |
| SH12 |  |  |  | + | + |
| SH25 |  |  |  |  |  |
| SH76 |  | + | + |  | + |

TABLE 8-continued

|  | BP953 | BP1151 | B1155 | BP1176 | Cocktail III |
| --- | --- | --- | --- | --- | --- |
| SH78 | + |  |  |  | + |
| SH79 |  |  |  |  |  |
| SH80 |  |  |  |  |  |
| SH81 | +/− |  |  |  | + |
| SH84 |  | +/− | +/− |  | + |
| SH86 |  |  | + |  | + |
| SH87 |  | + | + |  | + |
| SH88 |  | +/− |  | + | + |
| SH90 |  | + | +/− | + | + |
| SH92 |  |  |  | + | + |
| SH95 |  | +/− |  |  | + |
| SH96 |  | + |  |  | + |
| SH100 | + | + |  | +/− | + |
| SH102 | + | + |  | + | + |
| SH103 | + |  |  | +/− | + |
| SH104 |  |  |  | + | + |
| SH105 |  | + |  | + | + |
| SH107 |  |  |  |  |  |
| SH112 |  |  |  | + | + |
| SH113 |  | + |  | + | + |
| SH117 |  | +/− |  | + | + |
| SH118 |  |  | + |  | + |
| SH119 |  |  |  |  |  |
| SH120 | + |  |  | + | + |
| SH123 |  |  |  |  |  |

Example 3.4: Efficacy of Cocktail IV

As shown in the following Table 9, cocktail IV is able to destroy ST131 and BLSE-type *E. coli* strains.

TABLE 9

|  | BP700 | BP953 | BP970 | BP1002 | BP1176 | Cocktail IV |
| --- | --- | --- | --- | --- | --- | --- |
| ST131 TN03 | + | + | + | + | + | + |
| ST131 RD20873 |  | +/− |  |  | + | + |
| ST131 RD 5530 | + | + | +/− | +/− | + | + |
| ST131 XXF |  | +/− | +/− |  | + | + |
| ST131 XXT | + | + | +/− | + | + | + |
| ST131 6601 | + | + |  | + | + | + |
| ST131 27144 |  |  |  | + | + | + |
| ST131 28678 |  |  |  | +/− | + | + |
| ST131 30151 | + | + | +/− |  | + | + |
| BSE3 | + |  |  | + |  | + |
| BSE4 |  |  |  | + | +/− | + |
| BSE7 |  |  | + |  |  | + |
| BSE9 | +/− | + | +/− |  | + | + |
| BSE12 |  |  |  |  |  |  |

Example 3.5: Efficacy of Cocktail V

As shown in the following Table 10, cocktail V was able to destroy 100% meningitis-causing *E. coli* bacteria from R Debré collection.

TABLE 10

|  | BP1002 | BP1151 | BP1155 | BP1168 | BP1176 | BP1197 | Cocktail V |
| --- | --- | --- | --- | --- | --- | --- | --- |
| CFT073 | +/− | + |  |  |  |  | + |
| J96 | +/− | +/− |  |  | + |  | + |
| 536 | + | + | +/− | + |  | + | + |
| S5 | + | + | + | + |  | + | + |
| S11 | + | + | + | + |  | + | + |
| S12 | + | + | + | + | + | + | + |

TABLE 10-continued

| | BP1002 | BP1151 | BP1155 | BP1168 | BP1176 | BP1197 | Cocktail V |
|---|---|---|---|---|---|---|---|
| S13 | + | +/− | | | | | + |
| S15 | | + | | +/− | | | + |
| S22 | + | + | | | | | + |
| S25/C5 | + | +/− | | | | | + |
| S39 | + | + | | | + | | + |
| S41 | | +/− | +/− | + | + | + | + |
| S43 | + | +/− | | | | | + |
| S49 | + | | + | + | | + | + |
| S51 | | + | + | + | | + | + |
| S55 | +/− | + | | | + | | + |
| S63 | + | + | | | | | + |
| S69 | + | +/− | + | + | | + | + |
| S88 | +/− | +/− | +/− | +/− | +/− | +/− | + |
| S97 | +/− | + | +/− | +/− | + | +/− | + |
| S102 | | + | + | | + | + | + |
| S104 | +/− | + | | +/− | + | +/− | + |
| S105 | +/− | + | | | + | | + |
| S106 | +/− | + | + | + | + | + | + |
| S113 | + | + | | | + | | + |
| S120 | | +/− | | | | | + |
| S123 | +/− | + | | | +/− | | + |
| S124 | | + | | | + | | + |
| S130 | | +/− | | | + | | + |
| S133 | +/− | + | | | | | + |
| S138 | + | +/− | | | | | + |
| S149 | + | + | | | + | | + |
| S176 | +/− | +/− | | | | | + |
| S182 | + | + | | | + | | + |
| S191 | +/− | + | | | + | | + |
| S192 | + | + | | | + | | + |
| S242 | | + | | | + | | + |

Example 3.6: Efficacy of Cocktail VI

Cocktail VI is able to destroy nearly 96% of the 24 *E. coli* bacteria of ECOR collection as listed in table 2.

Example 3.7: Efficacy of Cocktails A and B

Cocktails A and B are both able to 100% of the 25 *E. coli* bacteria listed in table 2.

Bacteria were further enumerated and used to the calculation of resistance rate (number of bacteria after incubation/number of bacteria plated). Resistance rates with cocktail A comprising the 15 different types of bacteriophages are shown in the following table 11:

TABLE 11

| Bacteria | Rate (bacteria/ml) |
|---|---|
| ECOR1 | >1.00E−02 |
| ECOR24 | 2.00E−05 |
| ECOR60 | 4.00E−06 |
| S22 | 1.18E−04 |
| S106 | <1.00E−06 |
| S182 | 2.00E−06 |
| SH5 | 1.00E−06 |
| SH113 | 1.00E−06 |
| Astrid 9 | <1.00E−06 |
| BSE 3 | 8.50E−05 |
| BSE 7 | 5.00E−06 |
| 0157:133 | 2.63E−04 |
| XXT | 1.74E−04 |

All tested bacteria are sensitive to compositions of the invention.

Example 4: Cocktail Specificity

The cocktail specificity was confirmed by testing on ten bacteria species, including *Pseudomonas aeruginosa*, *Acinebacter baumanii*, *Enterobacter aerogenes* C, *Enterobacter asburiae*, *Enterobacter cloacae*, *Klebsiella pneumoniae*, *Proteus mirabilis*, *Staphylococus aureus*, *Stenotrophomonas maltophila*, *Serratia marcescens*.

Table 12 summarizes lytic activity observed for each bacteriophage used independently or in combination as a cocktail of 15 bacteriophages.

TABLE 12

| Bacterium | Phage | E54 EC 539 | E55 700 | E56 753 | E55 814 | E55 953 | E35 954 | DH5 970 | E56 1002 | E56 1151 | E59 1155 | E59 1168 | E60 1176 | DH5 1197 | E59 1226 | DH5 1229 | Cocktail 15 phages |
|---|---|---|---|---|---|---|---|---|---|---|---|---|---|---|---|---|---|
| *E. coli* | SH 213 | +/− | | | | | | +/− | +/− | +/− | + | + | + | +/− | + | + | + |
| | SH 141 | | | | | | | +/− | | | +/− | +/− | +/− | | +/− | | +/− |
| *Pseudomonas aeruginosa* | SH 85 | | | | | | | | | | | | | | | | − |
| | SH 224 | | | | | | | | | | | | | | | | − |
| *Acinebacter baumanii* | SH 32 | | | | | | | | | | | | | | | | − |
| | SH 34 | | | | | | | | | | | | | | | | − |
| *Enterobacter aerogenes C* | SH 97 | | | | | | | | | | | | | | | | − |
| | SH 98 | | | | | | | | | | | | | | | | − |
| *Enterobacter asburiae* | SH 74 | | | | | | | | | | | | | | | | − |
| *Enterobacter cloacae* | SH 111 | | | | | | | | | | | | | | | | − |
| | SH 121 | | | | | | | | | | | | | | | | − |
| *Klebsiella pneumoniae* | SH 89 | | | | | | | | | | | | | | | | − |
| | SH 283 | | | | | | | | | | | | | | | | − |
| *Proteus mirabilis* | SH 82 | | | | | | | | | | | | | | | | − |
| *Staphylococus aureus* | SH 14 | | | | | | | | | | | | | | | | − |
| | SH 129 | | | | | | | | | | | | | | | | − |
| *Stenotrophomonas maltophila* | SH 286 | | | | | | | | | | | | | | | | − |
| | SH 290 | | | | | | | | | | | | | | | | − |
| *Serratia marcescens* | SH 314 | | | | | | | | | | | | | | | | − |

The above table clearly show that no lytic activity on bacteria other than *E. coli* strain occurred. The bacteriophages and cocktail of the invention are therefore highly specific for *E. coli* strains.

Example 5: Efficiency of Bacteriophages on *E. coli* Strain In Vitro

Several strains of the EcoR collection were chosen to represent the genetic diversity of *E. coli* and various forms of antibiotic resistance. Strains were either sensitive or resistant to one or several antibiotics. They were grown individually or in combination with 2 to 8 strains. The bacteriophage cocktail was added at a MOI of 1 to $10^e$-6, i.e. at a dilution ratio (bacteria/phage) of 1 to 1 million.

The results are presented in FIG. 1 and in the following Table 13.

TABLE 13

Efficiency of bacteriophage cocktail obtained in vitro on *E. coli* mixture: at $2.10^{e7}$ cfu/ml and at various dilutions:

| Mix: | MOI 1 | MOI 0.1 | MOI 0.01 | MOI 0.001 | MOI 0.0001 | MOI 0.000001 |
| --- | --- | --- | --- | --- | --- | --- |
| 1 bacterium | ++ | ++ | ++ | ++ | + | + |
| 2 bacteria | ++ | ++ | + | +/− | +/− | +/− |
| 3 bacteria | ++ | ++ | + | + | +/− | +/− |
| 4 bacteria | ++ | ++ | ++ | + | +/− | +/− |
| 5 bacteria | ++ | ++ | ++ | + | + | +/− |
| 6 bacteria | ++ | ++ | + | +/− | +/− | +/− |
| 7 bacteria | ++ | ++ | ++ | + | +/− | +/− |
| 8 bacteria | ++ | ++ | ++ | + | +/− | |

The compositions of the invention are able to kill a mixture of 8 distinct strains of *E. coli* bacteria. The cocktail remains efficient against 8 strains at a dilution of 1/1000.

Example 6: Efficiency of Bacteriophages on *E. coli* Strain In Vivo

An isolated SH113 strain, collected on a burned patient in 2011, was used for the following experiments.

SH113 strain is resistant to ampicillin, ticarcillin, cefalotin, cefotaxim, nalidixic acid, norfloxacin, ofloxacin, ciprofloxacin.

SKH1 mouse (or hairless mouse) was used as mouse model of *E. coli* infection.

Modus Operandi: (See Table 14 Below)

Mice were immunodepressed by 3 IP injections of 1.5 mg of cyclophosphamide (Cy), every 2 days from the Day −3 before infection.

Mice were burned on skin by 2 μl of liquid yperite at 30 mg/kg.

Infection two days after the burn by subcutaneous injection of a bacterium suspension in burned site.

TABLE 14

| | Day | | | | |
| --- | --- | --- | --- | --- | --- |
| | −3 1.5 mg Cy | −2 Burn | −1 1.5 mg Cy | 0 Infection | 1 1.5 mg Cy |
| Injection route | IP | Yperite | IP | SC $10^7$ cfu | IP |
| PHAGE | | | | SC, IV or IP injection of cocktail (100 μl, i.e. | |

TABLE 14-continued

| | Day | | | | |
| --- | --- | --- | --- | --- | --- |
| | −3 1.5 mg Cy | −2 Burn | −1 1.5 mg Cy | 0 Infection | 1 1.5 mg Cy |
| | | | | $10^8$ PFU) 6 h post-infection | |

Cocktail compositions were prepared according to example 2 and compresses were soaked with bacteriophages cocktail at $10^{e7}$ phages/ml before applying at Day 0.

Figure 2:
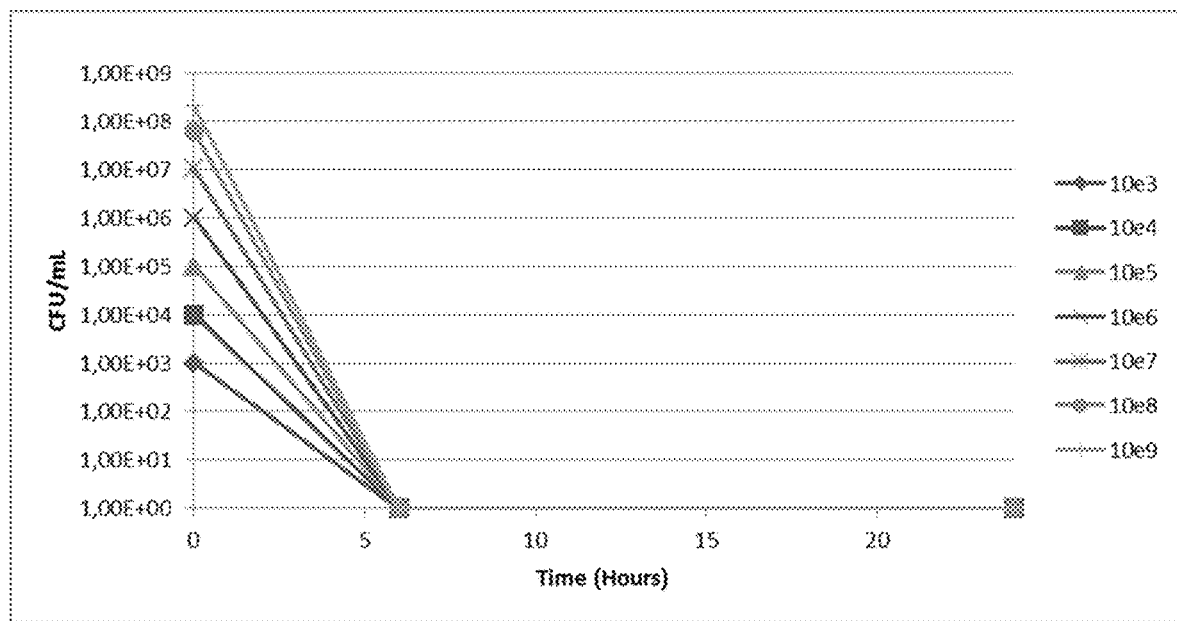
FIG. 2: In vivo efficacy of Bacteriophages of the invention on combinations of E. coli strains at various dosages.

Various concentrations of *E. coli* strains were tested with 100 μl of bacteriophage cocktail. As shown on FIG. 2, all *E. coli* strains were killed 6 h post-treatment.

Figure 3:
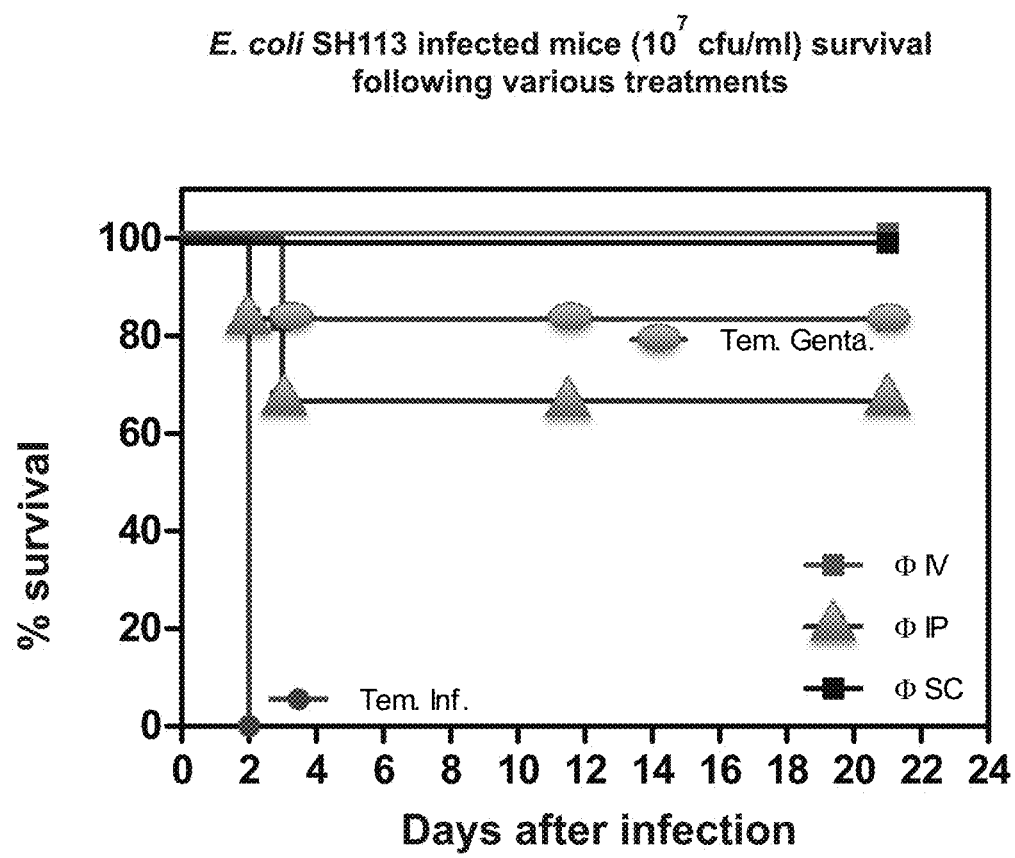
FIG. 3: Efficacy of bacteriophages of the invention on SH113 E. coli strain-mediated infection in vivo. Φ IV: intravenous treatment; Φ IP: intraperitoneal treatment; Φ SC: subcutaneous treatment; Temp Inf.: infected untreated control; Tem Genta.: infected gentamicin-treated control.

Upon administration of SH113 *E. coli* strain by subcutaneous injection to SKH1 mice, all mice died in the absence of further treatment. In the mice treated by injection of a bacteriophage cocktail as presented in table 9 above, a remarkable survival rate was observed (see FIG. 3): 100% survival for SKH1 mice treated subcutaneously or intravenously and 65% survival for intraperitoneal route treatment. By comparison, a 80% survival rate was observed for SKH1 mice treated by a double dose of gentamicin antibiotic at Day 0+6 h and during 7 consecutive days, including 2 injections on Day 1.

Figure 4:
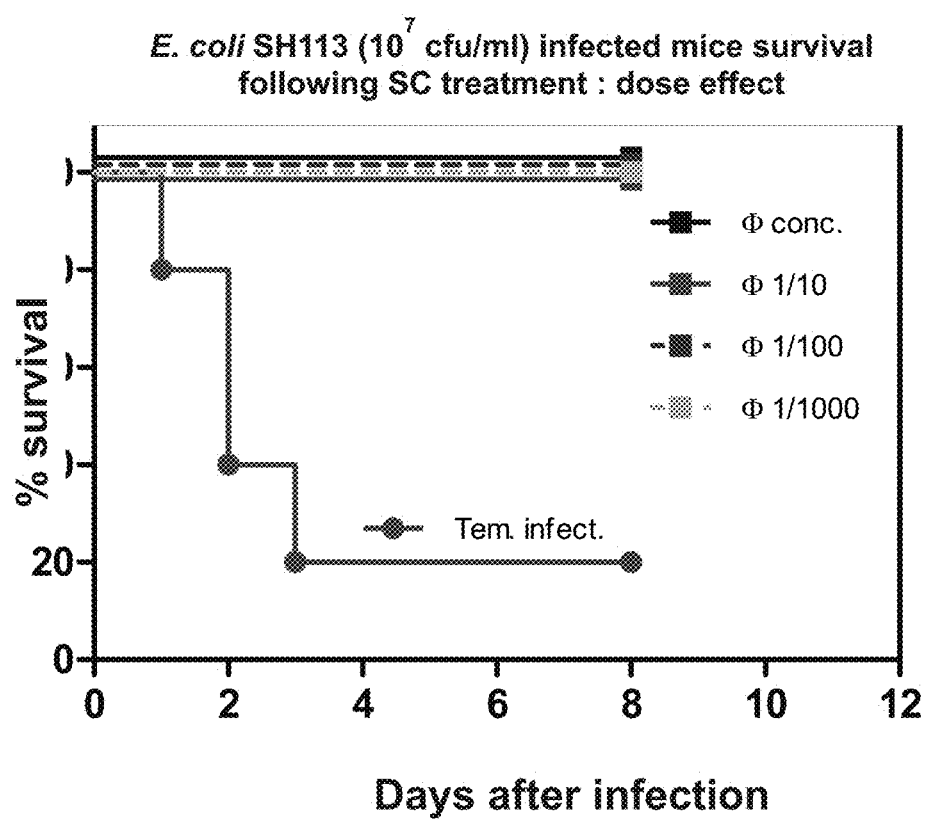
FIG. 4: Efficacy of bacteriophages of the invention on SH113 E. coli strain-mediated infection in vivo: dose effect. (conc.: full concentration ($10^8$ pfu/ml); Φ 1/10: 10 fold diluted concentration; Φ 1/100: 100 fold diluted concentration; Φ 1/1000: 1000 fold diluted concentration; Tem infect.: infected antibiotic treated control.

A remarkable 100% survival rate was also obtained after subcutaneous treatment with 1/10, 1/100 and 1/1000 (i.e. $10^5$ PFU per mouse) dilutions of the cocktail of the invention (see FIG. 4).

Accordingly, the compositions of the invention can treat an infection in vivo and can induce a 100% survival rate in infected mice.

REFERENCES

Afifi, R. Y., and A. A. El-Hindawi. 2008. Acute necrotizing fasciitis in Egyptian patients: a case series. Int. J. Surg. 66-14.

Brzozowski D., and D. C. Ross. 1997. Upper limb *Escherichia coli* cellulitis in the immunocompromised. J. Hand Surg. 22678-680.

Clark W A, 1962, Appl Microbiol. Comparison of several methods for preserving bacteriophages. 1962 September; 10:466-71.

Corredoira, J. M., J. Ariza, R. Pallares, J. Carratala, P. F. Viladrich, G. Rufi, R. Verdaguer, and F. Gudiol. 1994. Gram-negative bacillary cellulitis in patients with hepatic cirrhosis. Eur. J. Clin. Microbiol. Infect. Dis. 1319-24.

Drulis-Kawa Z, Majkowska-Skrobek G, Maciejewska B, Delattre A S, 2012, Learning from bacteriophages—advantages and limitations of phage and phage-encoded protein applications.; 13(8):699-722.

Fraser, N., B. W. Davies, and J. Cusack. 2006. Neonatal omphalitis: a review of its serious complications. Acta Paediatr. 95519-522.

Krebs, V. L., K. M. Koga, E. M. Diniz, M. E. Ceccon, and F. A. Vaz. 2001. Necrotizing fasciitis in a newborn infant: a case report. Rev. Hosp. Clin. Fac. Med. Sao Paulo 5659-62.

Needleman S B, Wunsch C D "A general method applicable to the search for similarities in the amino acid sequence of two proteins." 1970 March; 48(3):443-53.

Rodgers, G. L., J. Mortensen, M. C. Fisher, A. Lo, A. Cresswell, and S. S. Long. 2000. Predictors of infectious complications after burn injuries in children. Pediatr. Infect. Dis.; 19(10):990-5.

Stone R. 2002. Bacteriophage therapy. Stalin's forgotten cure. Science 298, 728-731 (DOI: 10.1126/science.298.5594.728).

Tourmousoglou, C. E., E. C. Yiannakopoulou, V. Kalapothaki, J. Bramis, and J. St. Papadopoulos. 2008. Surgical-site infection surveillance in general surgery: a critical issue. J. Chemother. 20(3)312-318.

Weinbauer M G. Ecology of prokaryotic viruses. FEMS Microbiol Rev 2004; 28:127-81.

SEQUENCE LISTING

The patent contains a lengthy sequence listing. A copy of the sequence listing is available in electronic form from the USPTO web site (https://seqdata.uspto.gov/?pageRequest=docDetail&DocID=US11957724B2). An electronic copy of the sequence listing will also be available from the USPTO upon request and payment of the fee set forth in 37 CFR 1.19(b)(3).

We claim:

1. An antibacterial composition comprising at least one bacteriophage having lytic activity to an *Escherichia coli* (*E. coli*) strain and a pharmaceutically acceptable excipient or carrier, said at least one bacteriophage being selected from the bacteriophages having a genome comprising a nucleotide sequence selected from any one of SEQ ID NOs: 1 to 15 or a sequence having at least 99% identity thereto, and said pharmaceutically acceptable excipient or carrier comprising a preservative in an amount effective to preserve the activity of the bacteriophage.

2. The composition of claim 1, comprising at least one of the bacteriophages BP539, BP700, BP753, BP814, BP953, BP954, BP970, BP1002, BP1151, BP1155, BP1168, BP1176, BP1197, BP1226 and BP1229 comprising the nucleotide sequence of SEQ ID NOs: 1 to 15, respectively.

3. The composition of claim 1, which is lytic against antibiotic-resistant *E. coli* strains.

4. The composition of claim 1, which is lytic against more that 90% of all bacterial strains of EcoR collection.

5. The composition of claim 1, which is a liquid, semi-liquid, solid or lyophilized formulation.

6. The composition of claim 1, which comprises between $10^{e2}$ and $10^{e12}$ PFU of bacteriophage.

7. The composition of claim 1, wherein the bacteriophage has lytic activity to a pathogenic *E. coli* strain, and wherein the bacteriophage (i) is specific for *E. coli* (ii) is active against antibiotic-resistant *E. coli* strains, and (iii) has a productive lytic effect ("PLE") below 15.

8. A method of treatment of an infection in a mammal in need thereof, comprising administering to the mammal infected with an *Escherichia coli* (*E. coli*) strain an antibacterial composition in an amount effective to treat the *E. coli* infection, wherein said composition comprises at least one bacteriophage having lytic activity to the *E. coli* strain, said at least one bacteriophage being selected from the bacteriophages having a genome comprising a nucleotide sequence selected from any one of SEQ ID NOs: 1 to 15 or a sequence having at least 99% identity thereto.

9. A method for improving the condition of a mammal by modifying the microbial flora thereof, comprising administering to the mammal an effective amount of an antibacterial composition, wherein said composition comprises at least one bacteriophage having lytic activity to an *Escherichia coli* (*E. coli*) strain, said at least one bacteriophage being selected from the bacteriophages having a genome comprising a nucleotide sequence selected from any one of SEQ ID NOs: 1 to 15 or a sequence having at least 99% identity thereto, and said microbial flora comprises the *E. coli* strain.

10. A method for decontaminating a material, comprising exposing the material to an amount of an antibacterial composition effective to decontaminate the material, wherein said composition comprises at least one bacteriophage having lytic activity to an *Escherichia coli* (*E. coli*) strain, said at least one bacteriophage being selected from the bacteriophages having a genome comprising a nucleotide sequence selected from any one of SEQ ID NOs: 1 to 15 or a sequence having at least 99% identity thereto, and said material is contaminated with the *E. coli* strain.

11. A method for preparing an antibacterial composition, comprising:
   a) producing at least one bacteriophage having lytic activity to an *Escherichia coli* (*E. coli*) strain, said at least one bacteriophage being selected from the bacteriophages having a genome comprising a nucleotide sequence selected from any one of SEQ ID NOs: 1 to 15 or a sequence having at least 99% identity thereto; and
   b) combining at least said bacteriophage with a pharmaceutically acceptable carrier or excipient, said pharmaceutically acceptable excipient or carrier comprising a preservative in an amount effective to preserve the activity of the bacteriophage.

12. A method for predicting or determining the efficacy of a bacteriophage therapy in a subject and treating said subject, wherein the method comprises:
   a) determining in vitro a lytic activity of a composition comprising at least one bacteriophage to an *E. coli* strain from a sample of said subject, said at least one bacteriophage having lytic activity to an *Escherichia coli* (*E. coli*) strain and being selected from the bacteriophages having a genome comprising a nucleotide sequence selected from any one of SEQ ID NOs: 1 to 15 or a sequence having at least 99% identity thereto; and b) treating the subject with the composition, when in step a) a lytic activity of said composition to at least one *E. coli* strain from said sample has been determined.

13. A method for selecting a subject or determining whether a subject is susceptible to benefit from a bacteriophage therapy and treating said subject, wherein the method comprises:

a) determining a lytic activity of a composition comprising at least one bacteriophage to an *E. coli* strain from a sample of said subject, said at least one bacteriophage having lytic activity to an *Escherichia coli* (*E. coli*) strain and being selected from the bacteriophages having a genome comprising a nucleotide sequence selected from any one of SEQ ID NOs: 1 to 15 or a sequence having at least 99° A identity thereto; and b) treating the subject with the composition, when in step a) a lytic activity of said composition to at least one *E. coli* strain from said sample has been determined.

* * * * *

UNITED STATES PATENT AND TRADEMARK OFFICE
CERTIFICATE OF CORRECTION

PATENT NO.       : 11,957,724 B2
APPLICATION NO.  : 17/038442
DATED            : April 16, 2024
INVENTOR(S)      : Flavie Pouillot and Hélène Blois It is certified that error appears in the above-identified patent and that said Letters Patent is hereby corrected as shown below:

In the Specification

Column 5,
Line 23, "(conc.:" should read --Φ conc.:--.

Column 19,
Line 60, "$10^{e2}$ and $10^{e2}$" should read --$10^{e2}$ and $10^{e12}$--.

Column 22,
Line 37, "0.2 m filter" should read --0.2 μm filter--.

Column 29,
Line 14, "to $10^{e}$-6" should read --to $10^{e-6}$--.

In the Claims

Column 33,
Line 22, "99° A identity" should read --99% identity--.

Signed and Sealed this
Twelfth Day of November, 2024

Katherine Kelly Vidal
*Director of the United States Patent and Trademark Office*